(12) United States Patent
Cai et al.

(10) Patent No.: US 7,091,345 B2
(45) Date of Patent: Aug. 15, 2006

(54) AMINO-SUBSTITUTED DIHYDROPYRIMIDO[4,5-D]PYRIMIDINONE DERIVATIVES

(75) Inventors: Jianping Cai, West Caldwell, NJ (US); Nikolaos Dimoudis, Wielenbach (DE); Konrad Honold, Penzberg (DE); Kin-Chun Luk, North Caldwell, NJ (US); Stefan Scheiblich, Penzberg (DE); Hilke Sudergat, Munich (DE); Georg Tiefenthaler, Sindelsdorf (DE); Oliver Tonn, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 285 days.

(21) Appl. No.: 10/697,543

(22) Filed: Oct. 30, 2003

(65) Prior Publication Data

US 2004/0087600 A1 May 6, 2004

(30) Foreign Application Priority Data

Nov. 4, 2002 (EP) .................... 02024573

(51) Int. Cl.
*C07D 471/04* (2006.01)
*C07D 491/113* (2006.01)
*A61K 31/519* (2006.01)

(52) U.S. Cl. ............... 544/256; 544/118; 544/230; 546/19; 514/234.2; 514/262.1

(58) Field of Classification Search ........... 544/230, 544/256, 118; 514/262.1, 234.2; 546/19
See application file for complete search history.

(56) References Cited

U.S. PATENT DOCUMENTS

| 4,473,560 A | 9/1984 | Biere |
| 4,503,049 A | 3/1985 | Biere |
| 4,784,993 A | 11/1988 | Bosies |
| 5,866,556 A | 2/1999 | Heikkila-Hoikka |

FOREIGN PATENT DOCUMENTS

| EP | 0 084 822 | 8/1983 |
| EP | 0 085 321 | 8/1983 |
| EP | 0 170 228 | 2/1986 |
| EP | 0 186 405 | 7/1986 |
| EP | 0 304 962 | 3/1989 |
| WO | WO 94/09017 | 4/1994 |
| WO | WO 99/61444 | 12/1999 |
| WO | WO 00/24744 | 5/2000 |
| WO | WO 01/29041 | 4/2001 |
| WO | WO 01/29042 | 4/2001 |
| WO | WO 01/44258 | 6/2001 |

OTHER PUBLICATIONS

Kinko, K. et al., Can. J. Chem. vol. 51 (1973) p. 333-337.
Merrifield, B. et al., Fed. Proc. Fed. Amer. Soc. Exp. Biol. vol. 21 (1962) p. 412.
Okuda, T. et al., J. Org. Chem. vol. 24 (1959) p. 14-16.
Ansel, H. et al., Pharm. Dosage Forms & Drug Delivery Systems (6th Ed.) 1995 p. 196.

*Primary Examiner*—Thomas C. McKenzie
(74) *Attorney, Agent, or Firm*—George W. Johnston; Patricia S. Rooha-Tramaloni

(57) ABSTRACT

Compounds of formula I

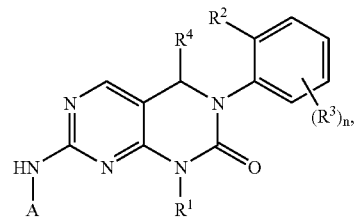

are described. These compounds are protein kinase inhibitors, in particular they inhibit the src family tyrosine kinases. Thus, these compounds are useful for the treatment of diseases mediated by src tyrosine kinases, including cell proliferative disorders such as cancer. Also described are methods of making and using compounds of formula I as well as pharmaceutical compositions containing these compounds.

39 Claims, No Drawings

AMINO-SUBSTITUTED DIHYDROPYRIMIDO[4,5-D]PYRIMIDINONE DERIVATIVES

FIELD OF THE INVENTION

The present invention relates to novel bicyclic-substituted dihydropyrimido[4,5-d]pyrimidinones. These compounds and their pharmaceutically acceptable salts are useful in the treatment or control of cell proliferative disorders, including cancer. The present invention also relates to a process for the manufacture of the compounds of the invention, pharmaceutical compositions containing these compounds, as well as methods of using these compounds to treat cell proliferative disorders.

BACKGROUND OF THE INVENTION

Protein kinases are known to mediate cell proliferation. Inhibition of such kinases is useful in the treatment of cell proliferative diseases.

Some substituted bicyclic nitrogen heterocycles are known in the art for their protein kinase, specifically tyrosine kinase, inhibitory activity. WO 01/29042 and WO 01/29041 relates to alkylamino-substituted dihydropyrimido[4,5-d] pyrimidinone derivatives with p38 inhibitory activity. WO 99/61444 relates to dihydropyrimido[4,5-d]pyrimidinones, substituted with aryl and hetarylamines, sulfides, sulfoxides and sulfones as inhibitors for cyclin-dependent kinases (cdks) and tyrosine kinases. Aryl and heteroarylamine substituted dihydropyrimido[4,5-d]pyrimidinones are also discussed in WO 00/24744 as inhibitors of T-cell tyrosine kinase p56$^{lck}$.

There continues to be a need for easily synthesized, small-molecule compounds effective in inhibiting the catalytic activity of protein kinases.

SUMMARY OF THE INVENTION

The present invention relates to compounds of formula

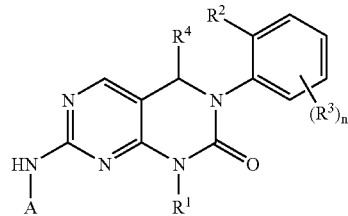

I wherein A, $R^1$, $R^2$, $R^3$ and $R^4$ are defined herein.

The compounds according to this invention show activity as protein kinase inhibitors, in particular src family tyrosine kinase inhibitors, and are therefore useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. Compounds of the present invention may be used as active agents in the prevention and therapy of, for example, transplant rejection, inflammatory bowel syndrome, rheumatoid arthritis, psoriasis, restenosis, allergic asthma, Alzheimers disease, Parkinson, stroke, osteoporosis, cancer, and benign hyperplasias.

The compounds of the present invention have surprisingly been found to show improved pharmacokinetic parameters in vivo, together with at least the same inhibitory activity against src-tyrosine kinases and therefore provide an enhanced bioavailability, compared to the compounds known in the art.

The present invention thus relates to compounds of formula I and their pharmaceutically acceptable salts and their enantiomeric forms, methods of preparation of these compounds, pharmaceutical compositions containing the compounds, as well as a method of using these compounds for the control, prevention or treatment of cell proliferative disorders, including the treatment or control of cancer, specifically solid tumors such as breast, colon or lung cancer.

DETAILED DESCRIPTION OF THE INVENTION

As used herein, the term "alkyl" alone means a straight-chain or branched-chain alkyl group containing from 1 to 6, preferably from 1 to 4, carbon atoms, such as methyl, ethyl, n-propyl, isopropyl, n-butyl, 2-butyl, tert-butyl, n-pentyl, n-hexyl as well as their isomers.

As used herein, the term "alkoxy" refers to a straight or branched chain hydrocarbonoxy group wherein the "alkyl" portion is an alkyl group as defined above. Examples include methoxy, ethoxy, propyloxy, i-propyloxy, n-butyloxy, 2-butyloxy, tert-butyloxy as well as n-pentyloxy and n-hexyloxy together with their isomers.

The term "alkoxyalkyl" means an alkyl group as defined above substituted by an alkoxy group as defined above, such groups are for example methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert-butyloxybutyl, methoxypentyl, ethoxypentyl, propyloxypentyl including their isomers.

The term "cycloalkyl" means a saturated, monocyclic ring containing 3 to 8, preferably from 3 to 6, carbon atoms, i.e. cyclopropyl, cyclobutyl, cyclopentyl, cyclohexyl, cycloheptyl or cyclooctyl.

In the term "alkoxycarbonyl" alkoxy has the meaning given above. Examples of such groups are methoxycarbonyl, ethoxycarbonyl, propoxycarbonyl, i-propoxycarbonyl, n-butoxycarbonyl, 2-butoxycarbonyl, tert-butoxycarbonyl as well as n-pentyloxycarbonyl and n-hexyloxycarbonyl together with their isomers.

The terms "acyl" and "acylamino" refer to groups R'—C(O)— and R'—C(O)—NH— in which R' is an alkyl group as defined above.

The term "aryl" as used herein denotes a phenyl and naphthyl, e.g. 1-naphthyl, 2-naphthyl.

The term "arylalkyl" as used herein denotes an aryl group as defined above attached to a straight chain alkylene group having 1 to 3 carbon atoms. Example of such groups are benzyl, 1-phenethyl, 2-phenethyl as well as phenpropyl and phenbutyl together with their isomers.

The term "heteroaryl" means a six or five membered aromatic ring which contains up to 3 heteroatoms selected independently from N, O or S. Examples for such heteroaryl groups are pyridyl, pyrimidyl, pyrazinyl, pyridazinyl, triazinyl, thienyl, imidazolyl, pyrazolyl, oxazolyl, isoxazolyl, thiazolyl, isothiazolyl, thiadiazolyl, oxadiazolyl, furanyl, triazolyl.

The term "heteroarylalkyl" as used herein denotes a heteroaryl group as defined above attached to a straight chain alkylene group having 1 to 3 carbon atoms.

All the aforementioned groups may optionally be substituted with halogen, hydroxy, cyano, nitro, amino, acylamino, alkyl, alkoxy, alkoxyalkyl, —$CONH_2$, —$SO_2NH_2$, —$S(O)_m$-alkyl (m=0, 1 or 2), —NH-alkyl, —$N(alkyl)_2$, —CONH(alkyl), $CON(alkyl)_2$, —$SO_2NH(alkyl)$, —$SO_2N(alkyl)_2$.

The term "effective amount" or "therapeutically effective amount" means an amount of at least one compound of the invention, or a pharmaceutically acceptable salt thereof, that significantly inhibits cells proliferation, such as proliferation of tumor cells.

The term "halogen" means fluorine, chlorine, bromine or iodine.

The term "pharmaceutically acceptable," such as pharmaceutically acceptable carrier, excipient, adjuvant etc., means pharmacologically acceptable and substantially non-toxic to the patient to which the particular compound is administered.

In one embodiment, the invention relates to compounds of formula I

I wherein
$R^1$ represents hydrogen or
alkyl, cycloalkyl, aryl, heteroaryl, arylalkyl or heteroarylalkyl, each of which may be optionally substituted with halogen, hydroxy, cyano, nitro, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), $CON(alkyl)_2$, —$SO_2NH(alkyl)$, —$SO_2N(alkyl)_2$;
$R^2$ represents halogen, cyano or $CF_3$;
$R^3$ each $R^3$ is independently selected from halogen, hydroxy, cyano, nitro, amino, acylamino, —$CONH_2$, —$SO_2NH_2$, —$S(O)_m$-alkyl, —NH-alkyl, —$N(alkyl)_2$, —CONH(alkyl), —$CON(alkyl)_2$, —$SO_2NH(alkyl)$, —$SO_2N(alkyl)_2$, or
alkyl, alkoxy or alkoxyalkyl, each of which may be optionally substituted with halogen, hydroxy, cyano, nitro, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), $CON(alkyl)_2$, —$SO_2NH(alkyl)$, —$SO_2N(alkyl)_2$;

$R^4$ represents hydrogen, alkyl, alkoxy or cyano;
A is selected from the group

A-1

A-2

A-3

A-4

A-5

A-6

$R^5$ is hydrogen, halogen, hydroxy, cyano, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), —$CON(alkyl)_2$, —$SO_2NH(alkyl)$ or —$SO_2N(alkyl)_2$;

$R^6$, $R^{6'}$ are each independently selected from hydrogen, alkyl or oxo;

$R^7$ is hydrogen, acyl, alkoxycarbonyl, alkoxyalkyl, alkyl or
alkyl substituted with hydroxy, cyano, —S(O)$_m$-alkyl,
amino, —NH-alkyl or —N(alkyl)$_2$;

$R^8$, $R^{8'}$ are each independently selected from hydrogen, oxo,
alkoxy, alkoxyalkyl, alkyl or alkyl substituted with hydrogen, hydroxy, cyano, pyrrolidin-
1-yl, morpholino, piperazin-1-yl, 4-alkyl-piperazin-1-yl,
piperidin-1-yl, —S(O)$_m$-alkyl, or a group NR$^9$R$^{9'}$, provided that when either $R^8$ or $R^{8'}$ represent an oxo group,
this oxo group is not adjacent to an S(O)$_m$ group;

$R^9$ and $R^{9'}$ are each independently selected from hydrogen,
alkyl or cycloalkyl;

X is oxygen or S(O)$_m$;

the dashed line is an optional second chemical bond;

n is 0, 1 or 2;

m is 0, 1 or 2; and p is 0, 1 or 2;

or a pharmaceutically acceptable salt or N-oxides thereof.

In another embodiment, the invention relates to compounds of formula I

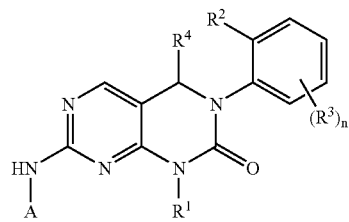

I wherein $R^1$ represents hydrogen or alkyl, cycloalkyl, aryl, heteroaryl, arylalkyl or heteroarylalkyl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), —SO$_2$N(alkyl)$_2$;

$R^2$ represents halogen, cyano or CF$_3$;

$R^3$ each $R^3$ is independently selected from halogen, hydroxy, cyano, nitro, amino, acylamino, —CONH$_2$, —SO$_2$NH$_2$, —S(O)$_m$-alkyl, —NH-alkyl, —N(alkyl)$_2$, —CONH(alkyl), —CON(alkyl)$_2$, —SO$_2$NH(alkyl), —SO$_2$N(alkyl)$_2$, or alkyl, alkoxy or alkoxyalkyl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), —SO$_2$N(alkyl)$_2$;

$R^4$ represents hydrogen, alkyl, alkoxy or cyano;

A is selected from the group

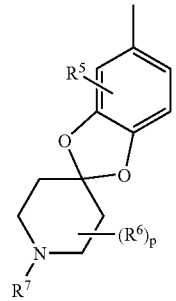

A-1

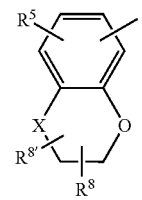

A-2

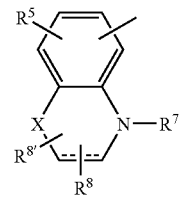

A-3

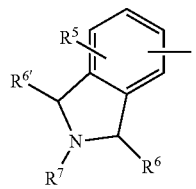

A-4

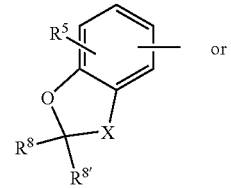

A-5 or

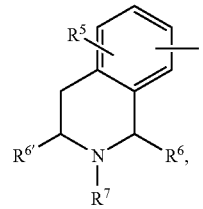

A-6

$R^5$ is hydrogen, halogen, hydroxy, cyano, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), —CON(alkyl)$_2$, —SO$_2$NH(alkyl) or —SO$_2$N(alkyl)$_2$;

$R^6$, $R^{6'}$ are each independently selected from hydrogen, alkyl or oxo;

$R^7$ is hydrogen, acyl, alkoxycarbonyl, alkoxyalkyl, alkyl or alkyl substituted with hydroxy, cyano, —S(O)$_m$-alkyl, amino, —NH-alkyl or —N(alkyl)$_2$;

$R^8$, $R^{8'}$ are each independently selected from hydrogen, oxo, alkoxy, alkoxyalkyl, alkyl or alkyl substituted with hydrogen, cyano, pyrrolidin-1-yl, morpholino, piperazin-1-yl, 4-alkyl-piperazin-1-yl, piperidin-1-yl, —S(O)$_m$-alkyl, or a group $NR^9R^{9'}$, provided that when either $R^8$ or $R^{8'}$ represent an oxo group, this oxo group is not adjacent to an $S(O)_m$ group;

$R^9$ and $R^{9'}$ are each independently selected from hydrogen, alkyl or cycloalkyl;

X is oxygen or $S(O)_m$;

the dashed line is an optional second chemical bond;

n is 0, 1 or 2;

m is 0, 1 or 2; and p is 0, 1 or 2;

or a pharmaceutically acceptable salt or N-oxide thereof.

Another embodiment of the invention contemplates compounds of formula I wherein $R^2$ represents bromine and n=0.

Another embodiment of the invention contemplates compounds of formula I wherein $R^2$ and $R^3$ are each independently selected from fluorine, chlorine, bromine or iodine and n=1. Preferred are compounds of formula I wherein $R^2$ represents bromine and $R^3$ represents fluorine. Most preferably $R^3$ is located at the 6-position of the phenyl ring. Also preferred are the compounds of formula I wherein $R^2$ and $R^3$ both represent chlorine and n=1.

Another embodiment of the invention contemplates compounds, wherein

A is a group selected from formula A-1, A-2, A-3, A-4, A-5 or A-6 as defined above;

$R^1$ is optionally substituted alkyl or aryl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), —CON(alkyl)$_2$, —SO$_2$NH(alkyl), —SO$_2$N(alkyl)$_2$;

$R^2$ is halogen or cyano;

$R^3$ each $R^3$ is independently selected from halogen;

n is 0 or 1;

$R^5$ is hydrogen; and $R^4$ hydrogen or methyl; or a pharmaceutically acceptable salt thereof.

Such compounds are for example:

7-(benzo[1,3]dioxol-5-ylamino)-3-(2,4-dichloro-phenyl)-1-(4-methoxy-phenyl)-3,4-dihydro-1H-pyrimido[4,5-d]pyrimidin-2-one or 2-[7-(4,4-Dioxo-3,4-dihydro-2H-4λ$^6$-benzo[1,4]oxathiin-6-ylamino)-1-methyl-2-oxo-1,4-dihydro-2H-pyrimido[4,5-d]pyrimidin-3-yl]-benzonitrile.

Another embodiment of the invention contemplates compounds of formula I, wherein A is a group A-1 as defined above.

Especially preferred are compounds of formula I, wherein

A is a group A-1;

$R^5$ is hydrogen;

$R^7$ is as defined above;

p is 0;

$R^1$ is alkyl;

$R^2$ is halogen;

$R^3$ is halogen;

n is 0 or 1; and $R^4$ is hydrogen;

or a pharmaceutically acceptable salt thereof.

Such compounds include:

3-(2-bromo-phenyl)-3,4-dihydro-7-(1'-acetyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one, 3-(2-bromo-6-fluorophenyl)-3,4-dihydro-7-(1'-acetyl-spiro[1,3-benzodioxolo-2,4'-piperidine]-5-yl)amino-1-methyl-pyrimido[4,5-d]pyrimidin-2(1H)-one, 3-(2-bromo-6-fluorophenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-ethyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-(2-methoxyethyl)-spiro[1,3-benzodioxolo-2,4'-piperidine]-5-yl)amino-1-methyl-pyrimido[4,5-d]pyrimidin-2(1H)-one, 3-(2-bromo-6-fluorophenyl)-3,4-dihydro-7-(1'-(2-methoxyethyl)-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-methyl-spiro[1,3-benzodioxolo-2,4'-piperidine]-5-yl)amino-1-methyl-pyrimido[4,5-d]pyrimidin-2(1H)-one, 3-(2-bromo-6-fluoro-phenyl)-3,4-dihydro-7-(spiro[1,3-benzodioxolo-2,4'-piperidine]-5-yl)amino-1-methyl-pyrimido[4,5-d]pyrimidin-2(1H)-one, 3-(2-bromo-6-fluoro-phenyl)-3,4-dihydro-7-(1'-methyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-cyanomethyl-spiro[1,3-benzodioxolo-2,4'-piperidine]-5-yl)amino-1-methyl-pyrimido[4,5-d]pyrimidin-2(1H)-one, and 3-(2-bromo-5-methoxyphenyl)-3,4-dihydro-7-(spiro[1,3-benzodioxolo-2,4'-piperidine]-5-yl)amino-1-methyl-pyrimido[4,5-d]pyrimidin-2(1H)-one.

A further preferred embodiment of the invention includes compounds of formula I wherein A is a group A-2 as defined above.

Especially preferred are compounds of formula I, wherein

A is a group A-2;

$R^5$ is hydrogen;

X is oxygen;

$R^8$, $R^{8'}$ are each independently selected from hydrogen or alkyl that optionally may be substituted with cyano, pyrrolidin-1-yl, morpholino, piperazin-1-yl, 4-alkyl-piperazin-1-yl, piperidin-1-yl, —S(O)$_m$-alkyl, or a group $NR^9R^{9'}$;

$R^9$ and $R^{9'}$ are each independently selected from hydrogen, alkyl or cycloalkyl;

$R^1$ is alkyl;

$R^2$ is halogen;

$R^3$ is halogen;

n is 0 or 1; and $R^4$ is hydrogen;

or a pharmaceutically acceptable salt thereof.

Examples of such compounds include:

3-(2-bromo-phenyl)-7-(2,3-dihydro-benzo[1,4]dioxin-6-ylamino)-1-methyl-3,4-dihydro-1H-pyrimido[4,5-d]pyrimidin-2-one, 3-(2-bromo-phenyl)-1-methyl-7-(2-pyrrolidin-1-ylmethyl-2,3-dihydro-benzo[1,4]dioxin-6-ylamino)-3,4-dihydro-1H-pyrimido[4,5-d]pyrimidin-2-one,
3-(2-bromo-phenyl)-1-methyl-7-(3-pyrrolidin-1-ylmethyl-2,3-dihydro-benzo[1,4]dioxin-6-ylamino)-3,4-dihydro-1H-pyrimido[4,5-d]pyrimidin-2-one,
3-(2-bromo-phenyl)-7-(2-dimethylaminomethyl-2,3-dihydro-benzo[1,4]dioxin-6-ylamino)-1-methyl-3,4-dihydro-1H-pyrimido[4,5-d]pyrimidin-2-one,
3-(2-bromo-6-fluoro-phenyl)-7-(2-dimethylaminomethyl-2,3-dihydro-benzo[1,4]dioxin-6-ylamino)-1-methyl-3,4-dihydro-1H-pyrimido[4,5-d]pyrimidin-2-one,
3-(2-bromo-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one,
3-(2-bromo-6-fluoro-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one,
3-(2-bromo-phenyl)-7-(2-cyclopropylaminomethyl-2,3-dihydro-benzo[1,4]dioxin-6-ylamino)-1-methyl-3,4-dihydro-1H-pyrimido[4,5-d]pyrimidin-2-one,
3-(2-bromo-phenyl)-1-methyl-7-(2-morpholin-4-ylmethyl-2,3-dihydro-benzo[1,4]dioxin-6-ylamino)-3,4-dihydro-1H-pyrimido[4,5-d]pyrimidin-2-one,
3-(2-bromo-phenyl)-1-methyl-7-(3-morpholin-4-ylmethyl-2,3-dihydro-benzo[1,4]dioxin-6-ylamino)-3,4-dihydro-1H-pyrimido[4,5-d]pyrimidin-2-one,
3-(2-bromo-6-fluoro-phenyl)-1-methyl-7-(3-morpholin-4-ylmethyl-2,3-dihydro-benzo[1,4]dioxin-6-ylamino)-3,4-dihydro-1H-pyrimido[4,5-d]pyrimidin-2-one, and
3-(2-bromo-6-fluoro-phenyl)-1-methyl-7-(3-pyrrolidin-1-ylmethyl-2,3-dihydro-benzo[1,4]dioxin-6-ylamino)-3,4-dihydro-1H-pyrimido[4,5-d]pyrimidin-2-one.

Also especially preferred are compounds of formula I, wherein
A is a group A-2;
$R^5$ is hydrogen;
X is oxygen;
$R^8$ is hydrogen
$R^{8\prime}$ is alkyl substituted with hydroxy;
$R^1$ is alkyl;
$R^2$ is halogen;
$R^3$ is halogen;
n is 0 or 1; and
$R^4$ is hydrogen;

or a pharmaceutically acceptable salt thereof.
Examples of such compounds include:
3-(2-bromo-phenyl)-7-(2-hydroxymethyl-2,3-dihydro-benzo[1,4]dioxin-6-ylamino)-1-methyl-3,4-dihydro-1H-pyrimido[4,5-d]pyrimidin-2-one,
3-(2-bromo-phenyl)-7-(3-hydroxymethyl-2,3-dihydro-benzo[1,4]dioxin-6-ylamino)-1methyl-3,4-dihydro-1H-pyrimido[4,5-d]pyrimidin-2-one,
3-(2-bromo-6-fluoro-phenyl)-7-(3-hydroxymethyl-2,3-dihydro-benzo[1,4]dioxin-6-ylamino)-1-methyl-3,4-dihydro-1H-pyrimido[4,5-d]pyrimidin-2-one, and
3-(2-bromo-6-fluoro-phenyl)-7-(2-hydroxymethyl-2,3-dihydro-benzo[1,4]dioxin-6-ylamino)-1-methyl-3,4-dihydro-1H-pyrimido[4,5-d]pyrimidin-2-one.

Also especially preferred are compounds of formula I, wherein
A is a group A-2;
$R^5$ is hydrogen;
X is $S(O)_m$;
m is 0, 1 or 2;
$R^8$, $R^{8\prime}$ represent hydrogen;
$R^1$ is alkyl;
$R^2$ is halogen;
$R^3$ is halogen;
n is 0 or 1; and
$R^4$ is hydrogen; or a pharmaceutically acceptable salt thereof.
Such compounds include for example:
3-(2-bromo-phenyl)-7-(2,3-dihydro-benzo[1,4]oxathiin-7-ylamino)-1-methyl-3,4-dihydro-1H-pyrimido[4,5-d]pyrimidin-2-one,
3-(2-bromo-phenyl)-7-(4,4-dioxo-3,4-dihydro-2H-4$\lambda^6$-benzo[1,4]oxathiin-7-ylamino)-1-methyl-3,4-dihydro-1H-pyrimido[4,5-d]pyrimidin-2-one,
3-(2-bromo-6-fluoro-phenyl)-7-(4,4-dioxo-3,4-dihydro-2H-4$\lambda^6$-benzo[1,4]oxathiin-6-ylamino)-1-methyl-3,4-dihydro-1H-pyrimido[4,5-d]pyrimidin-2-one, and
3-(2-bromo-phenyl)-7-(4,4-dioxo-3,4-dihydro-2H-4$\lambda^6$-benzo[1,4]oxathiin-6-ylamino)-1-methyl-3,4-dihydro-1H-pyrimido[4,5-d]pyrimidin-2-one.

A further preferred embodiment of the invention includes compounds of formula I wherein A is a group A-3 as defined above.

Especially preferred are compounds of formula I, are those wherein
A is a group A-3;
$R^5$ is hydrogen;
$R^7$ is hydrogen or alkyl;
X is $S(O)_m$;
m is 0, 1 or 2;
$R^8$, $R^{8\prime}$ are each independently selected from hydrogen, oxo or alkoxy,
provided that when one of $R^8$, $R^{8\prime}$ is oxo the dashed line is absent, and provided further that when $R^8$ and $R^{8\prime}$ are selected from hydrogen or alkoxy the dashed line may represent an additional bond to form a double bond;
$R^1$ is alkyl;
$R^2$ is halogen;
$R^3$ is halogen;
n is 0 or 1; and
$R^4$ is hydrogen;

or a pharmaceutically acceptable salt thereof.
Such compounds are for example:
3-(2-bromo-phenyl)-1-methyl-7-(3-oxo-3,4-dihydro-2H-benzo[1,4]thiazin-7-ylamino)-3,4-dihydro-1H-pyrimido[4,5-d]pyrimidin-2-one,
3-(2-bromo-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one,
3-(2-bromo-phenyl)-1-methyl-7-(4-methyl-1,3-dioxo-1,2,3,4-tetrahydro-1$\lambda^4$-benzo[1,4]thiazin-7-ylamino)-3,4-dihydro-1H-pyrimido[4,5-d]pyrimidin-2-one,
3-(2-bromo-phenyl)-1-methyl-7-(4-methyl-3,4-dihydro-2H-benzo[1,4]thiazin-7-ylamino)-3,4-dihydro-1H-pyrimido[4,5-d]pyrimidin-2-one,
3-(2-bromo-phenyl)-1-methyl-7-(3-oxo-3,4-dihydro-2H-benzo[1,4]thiazin-6-ylamino)-3,4-dihydro-1H-pyrimido[4,5-d]pyrimidin-2-one,
3-(2-bromo-6-fluoro-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one,
3-(2-bromo-6-fluoro-phenyl)-1-methyl-7-(3-oxo-3,4-dihydro-2H-benzo[1,4]thiazin-6-ylamino)-3,4-dihydro-1H-pyrimido[4,5-d]pyrimidin-2-one,
3-(2-bromo-phenyl)-1-methyl-7-(4-methyl-3-oxo-3,4-dihydro-2H-benzo[1,4]thiazin-6-ylamino)-3,4-dihydro-1H-pyrimido[4,5-d]pyrimidin-2-one, 3-(2-bromo-phenyl)-7-(3-methoxy-4-methyl-1-oxo-1,4-di-hydro-1λ⁴-benzo[1,4]thiazin-7-ylamino)-1-methyl-3,4-dihydro-1H-pyrimido[4,5-d]pyrimidin-2-one,
3-(2-bromo-6-fluoro-phenyl)-1-methyl-7-(4-methyl-3-oxo-3,4-dihydro-2H-benzo[1,4]thiazin-6-ylamino)-3,4-dihydro-1H-pyrimido[4,5-d]pyrimidin-2-one,
3-(2-bromo-6-fluoro-phenyl)-1-methyl-7-(4-methyl-1,1-dioxo-1,2,3,4-tetrahydro-1λ⁶-benzo[1,4]thiazin-7-ylamino)-3,4-dihydro-1H-pyrimido[4,5-d]pyrimidin-2-one,
3-(2-bromo-phenyl)-1-methyl-7-(4-methyl-1H-dioxo-1,2,3,4-tetrahydro-1λ⁶-benzo[1,4]thiazin-7-ylamino)-3,4-dihydro-1H-pyrimido[4,5-d]pyrimidin-2-one,
3-(2-bromo-phenyl)-1-methyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one, and
3-(2-bromo-6-fluoro-phenyl)-1-methyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one.

A further preferred embodiment of the invention includes compounds of formula I wherein A is a group A-4 as defined above.

Especially preferred are compounds of formula I, wherein
A is a group A-4;
$R^5$ is hydrogen;
$R^6$, $R^{6'}$ are each independently selected from hydrogen or oxo;
$R^7$ is hydrogen or alkyl that optionally may be substituted with hydroxy, cyano, —S(O)$_m$-alkyl, amino, —NH-alkyl or —N(alkyl)$_2$;
$R^1$ is alkyl;
$R^2$ is halogen;
$R^3$ is halogen;
n is 0 or 1; and
$R^4$ is hydrogen;

or a pharmaceutically acceptable salt thereof.

Such compounds include for example:
5-[6-(2-bromo-phenyl)-8-methyl-7-oxo-5,6,7,8-tetrahydro-pyrimido[4,5-d]pyrimidin-2-ylamino]-2-methyl-isoindole-1,3-dione,
3-(2-bromo-phenyl)-1-methyl-7-(2-methyl-2,3-dihydro-1H-isoindol-5-ylamino)-3,4-dihydro-1H-pyrimido[4,5-d]pyrimidin-2-one; hydrochloride salt,
5-[6-(2-bromo-phenyl)-8-methyl-7-oxo-5,6,7,8-tetrahydro-pyrimido[4,5-d]pyrimidin-2-ylamino]-isoindole-1,3-dione,
5-[6-(2-bromo-6-fluoro-phenyl)-8-methyl-7-oxo-5,6,7,8-tetrahydro-pyrimido[4,5-d]pyrimidin-2-ylamino]-2-methyl-isoindole-1,3-dione, and
3-(2-bromo-6-fluoro-phenyl)-7-[2-(2-hydroxy-1,1-dimethyl-ethyl)-2,3-dihydro-1H-isoindol-5-ylamino]-1-methyl-3,4-dihydro-1H-pyrimido[4,5-d]pyrimidin-2-one; hydrochloride.

A further preferred embodiment of the invention are the compounds of formula I wherein A is a group A-5 as defined above.

Especially preferred are compounds of formula I, wherein
A is a group A-5;
$R^5$ is hydrogen;
X is oxygen;
$R^8$, $R^{8'}$ are each independently selected from hydrogen or alkyl;
$R^1$ is alkyl;
$R^2$ is halogen;
$R^3$ is halogen;
n is 0 or 1; and
$R^4$ is hydrogen;

or a pharmaceutically acceptable salt thereof.

Such a compound is for example:
7-(benzo[1,3]dioxol-5-ylamino)-3-(2-bromo-phenyl)-1-methyl-3,4-dihydro-1H-pyrimido[4,5-d]pyrimidin-2-one.

Also especially preferred are compounds of formula I, wherein
A is a group A-5;
$R^5$ is hydrogen;
X is S(O)$_m$;
m is 0, 1 or 2;
$R^8$, $R^{8'}$ are each independently selected from hydrogen or alkyl;
$R^1$ is alkyl;
$R^2$ is halogen;
$R^3$ is halogen;
n is 0 or 1; and
$R^4$ is hydrogen;

or a pharmaceutically acceptable salt thereof.

Such compounds include for example:
3-(2-bromo-6-fluoro-phenyl)-7-(3,3-dioxo-2,3-dihydro-3λ⁶-benzo[1,3]oxathiol-5-ylamino)-1-methyl-3,4-dihydro-1H-pyrimido[4,5-d]pyrimidin-2-one, and
3-(2-bromo-phenyl)-7-(3,3-dioxo-2,3-dihydro-3λ⁶-benzo[1,3]oxathiol-5-ylamino)-1-methyl-3,4-dihydro-1H-pyrimido[4,5-d]pyrimidin-2-one.

A further preferred embodiment of the invention are the compounds of formula I wherein A is a group A-6 as defined above.

Especially preferred are compounds of formula I, wherein
A is a group A-6;
$R^5$ is hydrogen;
$R^6$, $R^{6'}$, $R^7$ have the significance given above;
$R^1$ is alkyl;
$R^2$ is halogen;
$R^3$ is halogen;
n is 0 or 1; and
$R^4$ is hydrogen;

or a pharmaceutically acceptable salt thereof.

Examples of such compounds include
3-(2-Bromo-5-methoxy-phenyl)-7-(4,4-dioxo-3,4-dihydro-2H-4λ⁶-benzo[1,4]oxathiin-ylamino)-1-methyl-3,4-dihydro-1H-pyrimido[4,5-d]pyrimidin-2-one,
7-(4,4-Dioxo-3,4-dihydro-2H-4λ⁶-benzo[1,4]oxathiin-6-ylamino)-3-(2-fluoro-6-methoxy-phenyl)-1-methyl-3,4-dihydro-1H-pyrimido[4,5-d]pyrimidin-2-one,
3-(2-Bromo-phenyl)-7-(4,4-dioxo-3,4-dihydro-2H-4λ⁶-benzo[1,4]oxathiin-6-ylamino)-1,4-dimethyl-3,4-dihydro-1H-pyrimido[4,5-d]pyrimidin-2-one; enantiomer 1,
3-(2-Bromo-phenyl)-7-(4,4-dioxo-3,4-dihydro-2H-4λ⁶-benzo[1,4]oxathiin-6-ylamino)-1,4-dimethyl-3,4-dihydro-1H-pyrimido[4,5-d]pyrimidin-2-one; enantiomer 2,
3-(2-Bromo-phenyl)-1,4-dimethyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one; enantiomer 2,
3-(2-Bromo-phenyl)-1,4-dimethyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one; enantiomer 1, and
2-[7-(4,4-Dioxo-3,4-dihydro-2H-4λ⁶-benzo[1,4]oxathiin-6-ylamino)-1-methyl-2-oxo-1,4-dihydro-2H-pyrimido[4,5-d]pyrimidin-3-yl]-3-fluoro-benzonitrile.

A further embodiment of the invention is the process for the manufacture of the present amino-substituted dihydropyrimido[4,5-d]pyrimidinone derivatives of formula I. Said compounds can be prepared a) by reacting a compound of the general formula

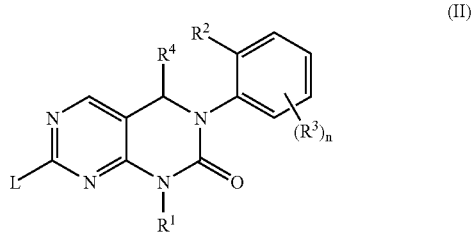

wherein $R^1$ to $R^4$ and n are as defined earlier, any hydroxy or amino group present may be in protected form, and L signifies a leaving group such as a sulfonyl derivative as for example benzylsulphonyl, phenylsulphonyl, alkanesulphonyl, a sulfonyloxy derivative as for example p-tolylsulfonyloxy, methanesulfonyloxy, or trifluoromethanesulfonyloxy, an alkanesulfinyl, or a halogen such as chloro, bromo, iodo, fluoro, with an amine of the general formula

wherein A is as defined earlier and, where required, deprotecting a protected ydroxyl or protected amino group present in the reaction product; or b) by reacting a compound of formula (II) with ammonia, or with an protected amine such as benzylamine and subsequently cleaving off the protecting group, to give the amino derivative of formula

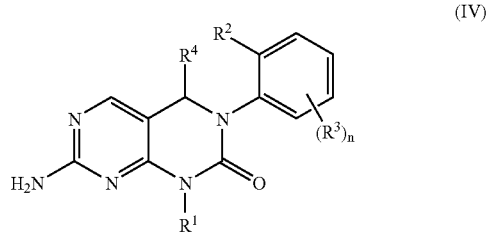

wherein the symbols are as defined above;

which is then be reacted with a bicyclic compound of formula

wherein L' represents a leaving group as defined for L, preferably a halogen such as chloro, bromo, iodo, or a sulfonyloxy derivative as for example p-tolylsulfonyloxy, methanesulfonyloxy, or trifluoromethanesulfonyloxy;

the reaction of (IV) with (V) may be catalysed by a transition metal catalyst known in the art, and c) if desired, converting a basic compound of formula I obtained into a pharmaceutically acceptable salt with an acid, or converting an acidic compound of formula I obtained into a pharmaceutically acceptable salt with a base, and d) if desired, converting a compound of formula I into a N-oxide by reaction oxidation with an oxidizing agent like 3-chloro-perbenzoic acid, trifluoroperacetic acid, or dimethyldioxiran.

The reaction of a compound of formula II with an amine of formula III in accordance with process (a) can be carried out in the presence or absence of a solvent. When a solvent is used, this can conveniently be a halogenated aliphatic hydrocarbon, e.g. dichloromethane or 1,2-dichloroethane, an open-chain ether, e.g. diethyl ether or diisopropyl ether or diethylene glycol dimethyl ether, a cyclic ether, e.g. tetrahydrofuran (THF), an optionally halogenated aromatic hydrocarbon, e.g. benzene, toluene, a xylene or chlorobenzene, or a formamide, e.g. dimethylformamide (DMF), or N-methylpyrrolidone (NMP) or dimethylsulfoxide (DMSO), or sulfolane. Suitably, the reaction is carried out at a temperature in the range of about 0° C. to about 200° C., preferably at about 100° C. to about 200° C. The reaction can be carried out in the presence of an acid, like hydrochloric acid (HCl), toluene sulfonic acid, trifluoro acetic acid, or mchlorobenzoic acid. Furthermore, the bicyclic anilines of formula III may be reacted as preformed salts. Alternatively, the reaction can be carried out in the presence of a base like potassium carbonate, triethyl amine, potassium tert-butoxide, sodium hydride, lithiumdiisopropylamide (LDA), buthyl lithium, or lithium hexamethyl disilazide. When using strong bases, the reaction may also be carried out at lower temperatures in the range from −20° C. to 50° C.

A hydroxy or amino or carboxylic acid group present in a starting material of formula II or III, may optionally be protected according to methods known in the art. A hydroxy group can for example be protected in the form of an ether, e.g. alkyl or silyl ether, or an ester, e.g. alkyl ester. With respect to protected amino, phthalimido is an example of such a group. An example of a protected carboxylic acid is an ester, e.g. alkyl ester.

Deprotection of such protected groups present in a product obtained by reacting a compound of formula II with an amine of formula III can be carried out in a manner known per se. Thus, for example, an ether such as an alkyl ether can be converted into hydroxy by treatment with hydrobromic acid; and an ester such as an alkyl ester can be converted into hydroxy using an alkali metal aluminium hydride such as lithium aluminium hydride. Again, for example, the phthalimido group can be converted into amino by treatment with hydrazine hydrate. A protected carboxylic acid group such as an ester, e.g. alkyl ester, can for example be converted into the free carboxylic acid group by cleaving it with an alkali metal hydroxide.

In the process according to b) a compound of formula II is reacted with ammonia or an protected amine to form the 2-amino-derivative of formula IV. The cleavage of an protecting group such the 4-methoxybenzyl group, can be carried out using methods which are known per se. For example, the cleavage can be carried out using trifluoroacetic acid, conveniently at an elevated temperature, preferably at the reflux temperature of the reaction mixture.

The 2-amino derivative of formula IV can be coupled to the bicyclic residue of formula V analogous to the method of WO2001 44258, e.g. by catalysis with a Pd-phosphine complex like Pd(OAc)$_2$/BINAP, Pd(dba)$_2$/P(tert-Bu)$_3$ or Xantphos, in the presence of a base like Cs$_2$CO$_3$, NaOtert-Bu, NaOPh, or K$_3$PO$_4$, in an inert solvent like toluene or xylene, or THF, or NMP, in the temperature range between 50 and 180° C.

Compounds of formula I, wherein A is a group A-1, A-2, A-3, A-4, A-5, or A-6 and one of the groups R$^7$, R$^8$ or R$^{8'}$ are an optionally substituted aminoalkyl group, can be prepared from the compounds of formula I bearing the corresponding hydroxy-alkyl substituent for example by a two step reaction by substitution of the hydroxy by halogen, or tosyloxy, in the presence of for example tosylchloride or thionyl chloride and subsequently reacting the chloride or tosylate with an optionally substituted amino group as depicted in reaction scheme I.

Scheme 1

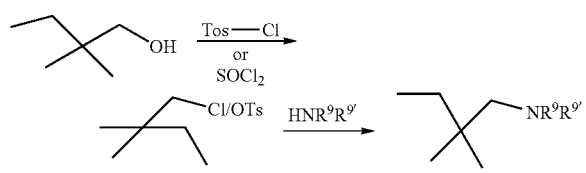

Compounds of formula I in which any of groups A-2, A-3 or A-5 or any of their substituents contain a sulfur atom in oxidized form —S(O)— or —S(O)$_2$—, may also be prepared by oxidation of the corresponding sulfanyl compounds formula I with 3-chloroperbenzoic acid (MCPBA), oxone, 2-phenylsulfonyl-3-phenyloxaziridine, sodium periodate or H$_2$O$_2$ in presence of a catalyst such as a W—, V—, or Mo compound, or other oxidation reagents known in the art according to standard procedures.

According to the process step c) basic compounds of formula I can form salts with inorganic acids, e.g. hydrohalic acids such as hydrochloric acid or hydrobromic acid, sulphuric acid, nitric acid or phosphoric acid, or with organic acids, e.g. formic acid, acetic acid, trifluoroacetic acid, citric acid, fumaric acid, malic acid, maleic acid, succinic acid, tartaric acid, salicylic acid, methanesulphonic acid, ethanesulphonic acid, 4-toluenesulphonic acid and the like. Acidic Compounds of formula I can form salts with bases e.g. inorganic bases such as alkali and alkaline earth metals or organic bases such as amines. Examples of inorganic bases are metals used as cations are sodium, potassium, magnesium, calcium and the like. Examples of suitable amines are ethylenediamine, 2-hydroxyethylamine, di(2-hydroxyethyl) amine, ethylamine and the like. These salts can be formed and isolated in a manner known per se. Salts of basic compounds of formula I with acids are preferred.

The starting materials of formula II, wherein L is an alkyl-, phenyl-, or benzylsulfonyl group are known from WO 00/24744. They can be prepared as illustrated in Scheme 2 for L=methylsulfonyl:

Scheme 2

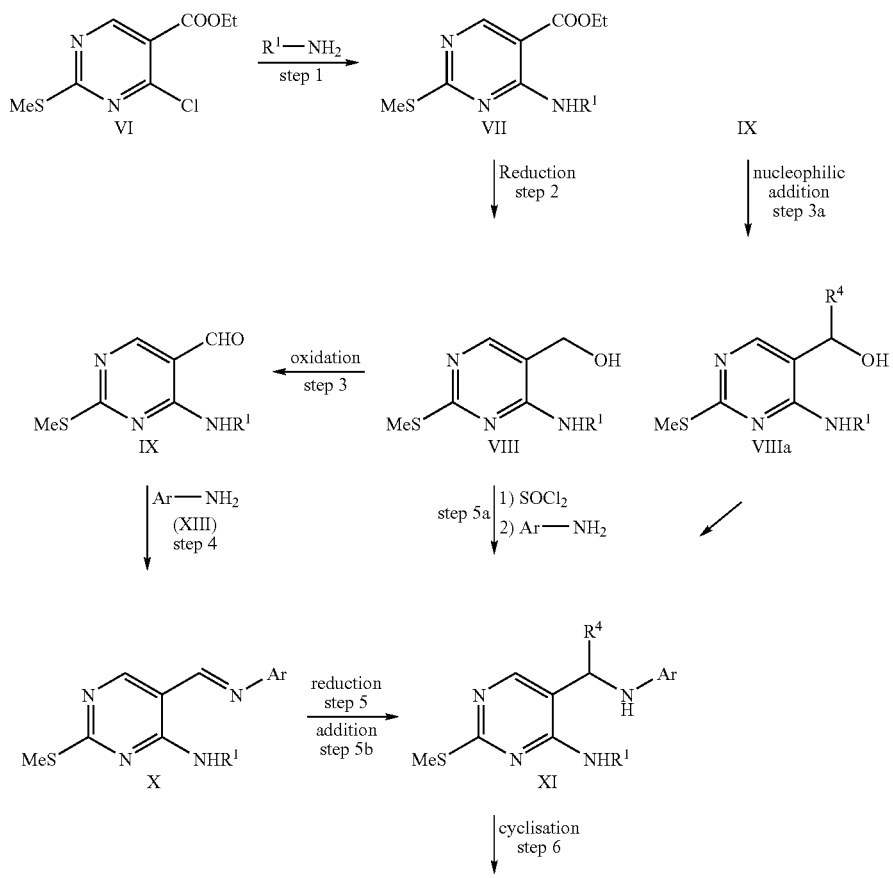

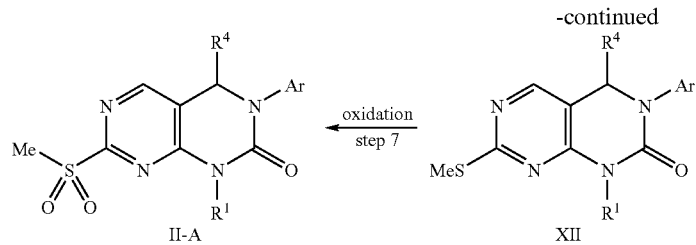

wherein R1 and R4 are as defined above and Ar is the residue

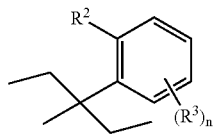

wherein $R^2$, $R^3$ and n are as defined above.

Step 1

A compound of formula VI is reacted with an amine $R_1$—$NH_2$ to give a compound of formula VII. This reaction is conveniently carried out in a solvent which is inert under the reaction conditions, preferably a halogenated aliphatic hydrocarbon, especially dichloromethane, an optionally halogenated aromatic hydrocarbon, an open-chain or cyclic ether, a formamide or a lower alkanol. Suitably, the reaction is carried out at about −20° C. to about 120° C.

Step 2

Step 2 comprises the reduction of a compound of formula VII to give an alcohol of formula VIII. This reduction is carried out using lithium aluminum hydride in a manner known per se, e.g. in a solvent which is inert under the conditions of the reduction, preferably an open-chain or cyclic ether, especially tetrahydrofuran, at about −20° C. to about 70° C., preferably at about 0° C. to about room temperature.

Step 3

Oxidation of an alcohol of formula VIII to a carboxaldehyde of formula IX. This oxidation is carried out with manganese dioxide in a manner known per se, conveniently in a solvent which is inert under the oxidation conditions, preferably a halogenated aliphatic hydrocarbon, especially dichloromethane, or an optionally halogenated aromatic hydrocarbon. Suitably, the oxidation is carried out at about 0° C. to about 60° C.

Step 3a

Nucleophilic addition to an aldehyde of the general formula 1×gives substituted alcohols of the general formula VIIIa. Such addition can be performed by an Grignard reagent like methyl or ethyl magnesium bromide in an inert solvent like ether or THF in a temperature range from 0° C. to reflux temperature. Other nucleophiles are e.g. trimethylsilyl cyanide or tributylstannyl cyanide which can be added to the aldehyde in an inert solvent like dichloromethane or toluene or THF. Alternatively, sodium cyanide can be used in the presence of acetic acid. These addition reactions can be carried out in a temperature from −20° C. to 150° C.

Step 4

Reaction of a carboxaldehyde of formula IX with an amine of formula XIII to give an imine of formula X. This reaction may be carried out in the presence of an acid, e.g. an aromatic sulphonic acid, preferably 4-toluenesulphonic acid, with azeotropic removal of the water formed during the reaction. Conveniently, the reaction is carried out in a solvent which is inert under the reaction conditions, preferably an optionally halogenated aromatic hydrocarbon, especially toluene, and at a temperature of about 70° C. to about 150° C., especially at the reflux temperature of the solvent.

Step 5

Step 5 comprises the reduction of the imine of formula X to give a compound of formula XI. This reduction is carried out using sodium borohydride, lithium aluminum hydride or sodium triacetoxyborohydride in a manner known per se. Preferably, the compound of formula X is not purified, but rather the reaction mixture in which it is prepared is concentrated and the concentrate obtained is taken up in a solvent which is inert under the conditions of the reduction, preferably an open-chain or cyclic ether, especially tetrahydrofuran or an optionally halogenated aromatic hydrocarbon or a lower alkanol, and then treated with an aforementioned reducing agent. The reduction is suitably carried out at about 0° C. to about 100° C., preferably at about 25° C.

Step 5a

Alternatively, conversion of the alcohol of formula VIII or VIIIa to the amine of formula XI can be accomplished by first chlorinating the alcohol of formula VIII or VIIIa with thionyl chloride analogous to Okuda, Price, J. Org. Chem. 24 (1959) 14; and substituting the chloro by an aromatic amine of formula XIII in an inert solvent like acetonitrile DMF, THF or NMP, optionally in the presence of a catalyst like sodium iodide. This substitution reaction may be carried out in the temperature range from 15° C. to 200° C., preferably between room temperature and 120° C.

Step 5b

Alternatively, in a fashion similar to step 3a, a nucleophilic addition to the imine of formula X can be performed to yield substituted amines of formula XI. The same reagents and conditions as described under step 3a are also suitable here. In addition, more reactive nucleophiles like methyl- or ethyl lithium may be used. The addition of silyl- or tin cyanide reagents to the imine may also be catalyzed by transition metal salts like $Yb(OTf)_3$ or $Zr(OtBu)_4$. In a special variant, the imine of formula X may be cyclised with phosgen in an inert solvent like benzene or dichloromethane, to give an intermediate of formula XII with $R^4$=Cl, as described by Kinko, K., et al., Can. J. Chem. 51(1973) 333–337. In such intermediates, said chlorine can be substituted by lower alkohols, suitably in the presence of a base like sodium bicarbonate, potassium carbonate, ethyl-di-isopropyl amine, or sodium hydride to give compounds of formula XII with $R^4$=alkoxy.

Step 6

Cyclisation of a compound of formula XI yields a compound of formula XII. This cyclisation is effected by reaction with phosgene or trichloromethyl chloroformate in a manner known per se, conveniently in the presence of a tertiary organic base, preferably a tri($C_1$–$C_6$-alkyl)amine, especially triethylamine, and in a solvent which is inert under the conditions of the reaction, preferably an open-chain or cyclic ether, especially THF, an optionally halogenated aromatic hydrocarbon or a halogenated aliphatic hydrocarbon. Alternatively, a phosgene equivalent like carbonyl diimidazole may be applied in the presence of a stronger base like sodium hydride or potassium tert-butoxide, in a solvent like THF, NMP, or DMF. Conveniently, the reaction is carried out at about −20° C. to about 50° C., preferably at about 0° C. to about room temperature.

Step 7

Oxidation of a compound of formula XII with 3-chloroperbenzoic acid yields a starting material of formula II-A, i.e. a compound of formula II wherein L is alkyl-$S(O)_m$. This oxidation is carried out in a manner known per se, conveniently in a solvent which is inert under the conditions of the oxidation, preferably a halogenated aliphatic hydrocarbon, especially dichloromethane, and at about −20° C. to about 50° C., preferably about 0° C. to about room temperature.

Compounds of formula XII in Scheme 2 or starting materials of formula II in which $R^1$ represents hydrogen can be N-substituted by treatment with an alkali metal hydride, especially sodium hydride, and subsequent reaction with a compound of the general formula $R^{1a}$-L"

wherein $R^{1a}$ has any of the values accorded to $R^1$ hereinbefore except hydrogen, aryl or heteroaryl and L" represents a leaving group as defined for L such as a sulfonyl derivative as for example benzylsulphonyl, phenylsulphonyl, alkanesulphonyl, a sulfonyloxy derivative as for example p-tolylsulfonyloxy, methanesulfonyloxy, or trifluoromethanesulfonyloxy, an alkanesulfinyl or a halogen such as chloro, bromo, iodo or fluoro. L" preferably represents iodo.

The N-substitution is conveniently carried out in a solvent which is inert under the reaction conditions, preferably a formamide, especially dimethylformamide, an open-chain or cyclic ether or an optionally halogenated aromatic hydrocarbon. Suitably, the reaction is carried out at about 50° C. to about 200° C., preferably at about 50° C. to about 150° C.

When $R^1$ includes a nitrogen-containing heteroaryl group, the process may lead to N-oxide formation. The N-oxides can be converted to the free N compounds by standard methods, for example, by reaction with triphenyl phosphine.

The starting materials of formula (III) and the amines $R^1$—NH2 are known or can be prepared by standard procedures know in the art. E.g. aromatic amines can be prepared from the corresponding nitro compounds by reduction with H2/Pd—C, Sn/HCl, or NaS2O4, or from the corresponding benzoic acid derivatives by Hoffmann or Curtius rearrangement.

The starting materials of formula (V) are known or can be prepared by standard procedures. E.g. if L is Cl or Br, it may be introduced by halogenation of the aromatic ring. If L is $OSO_2CF_3$, it may be prepared by reaction of the corresponding phenol with trifluoromethane sufonic acid anhydride or N,N-bis-trifluoromethylsulfonyl-anilin in the presence of a base.

Intermediates of formula III and V containing an oxo group in a ring of formula A-1 to A-6 can also be converted into the compounds of formulae III and V by reduction of the carbonyl moiety to a —$CH_2$— or —CHOH— moiety with e.g. $NaBH_4$, $LiAlH_4$, DIBAL or $BH_3SMe_2$. Such a reduction is suitably carried out in ether, THF or dichloromethane at temperatures ranging from 0° C. to 150° C. Alternatively, such a reduction reaction may also be performed with compounds of formula I.

Substituents $R^5$–$R^8$ on the groups A-1–A-6 can either be introduced into the starting materials of formula III or V, or alternatively be added subsequent to the reaction procedure to give the respective compounds of formula I. Said substituents my for example be introduced by reacting an amino- or a —$S(O)_m$—$CH_2$ moiety with an electrophile in the presence of a base. Suitable electrophiles are $C_1$–$C_6$-alkyl halides, e.g. MeI, aldehydes and ketones, e.g. formaldehyde or acetone, epoxides, e.g. oxirane, or acylating agents, e.g. acetic anhydride and the like. Suitable bases may be sodium hydride, potassium tert-butoxide, butyl lithium, triethyl amine, pyridine, potassium carbonate and the like. Hydroxyalkyl residues on a group A-1–A-6 in intermediates of formula III or IV, or in compounds of formula I, may be converted to a leaving group, e.g. a chloroalkyl or tosyloxyalkyl moiety, by standard procedures and subsequently substituted by cyanide, amines, alkohols, or thiols. Suitably, these substitution reactions can be carried out in the presence of a base like a sodium alkoxide, ethyl-di-isopropyl amine, potassium carbonate, or sodium hydride, in solvents like THF, DMF, NMP, DMSO, or ethanol, at temperatures ranging from 0° C. to 180° C.

In intermediates of formula III or IV and compounds of formula I, which contain sulfur atoms in unoxidized form, these sulfur atoms may be oxidized to sulfinyl and sulfonyl moieties by standard reagents, for instance 3-chloroperbenzoic acid, trifluoroperacetic acid, oxone, sodium periodate, sodium perborate, dimethyl oxirane, or hydrogen peroxide in the presence of a V or W or Ru catalyst.

Another embodiment of this invention are compounds of the general formula A-1-I,

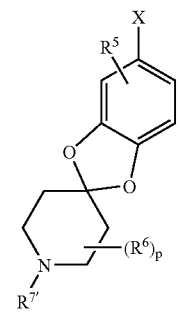

A-1-I wherein
$R^5$, $R^6$, $R^7$ and p have the significance given above; and
X is $NO_2$ or an optionally protected $NH_2$ group.

Yet another embodiment of the invention is the use of compounds of the general formula A-1-I as intermediates for the preparation of the compounds of the general formula I. Said $NH_2$ group can optionally be present in a protected form by using suitable protecting groups that are well known to the person skilled in the art.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available. As used herein the terms "enantiomer 1" and "enantiomer 2" denote the first and second eluting enantiomer respectively, when using a chiral phase Chiracel OD-CSP (commercial 20 µm material from Daicel, eluent heptane/iso-propanol 1:1) for the separation of the racemate. Consequently, this terminology is used for the starting materials or intermediates as well as for the final products resulting from the respective starting materials or intermediates.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Ansel, H., et. al., Pharmaceutical Dosage Forms and Drug Delivery Systems, 6th ed., 1995, pp. 196 and 1456–1457.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A preferred pharmaceutical preparation was obtained by using the following procedure:

1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 µm. The suspensions are suitable for oral applications and were used in the in vivo pharmacokinetic testings described below.

The activity of the compounds according to this invention as inhibitors for the src-family tyrosine kinases was shown by using the following assay.

SRC-Inhibitor-Assay Parameters:

| Reaction mixture: | |
|---|---|
| ATP | 5 µM |
| Peptide (Ro + Ja133 – Ro): | 10 µM |
| Ja133 – Ro | 196 nM |
| Ro | 9.8 µM |
| PT66 | 230 ng/ml |

Assay buffer: 4 mM MgCl2
2 mM TCEP
50 mM HEPES
0,1% Tween 20
pH 7.3

| Enzyme: | 2.5 U/ml |
|---|---|
| Inhibitor: | max. 25 µM |
| | min. 0.42 nM |

Material:

Eu-labelled phosphotyrosine antibody:—for Lck Cisbio Mab PT66-K, for Src EG&G Wallac PT66 Eu-W1024 (all commercially available).

Peptides: Ro: NH$_2$-A-E-E-E-I-Y-G-E-F-E-A-K-K-K-K-CONH$_2$, and Ja133-Ro: Ja133-G-Aminocaprylic acid-A-E-E-E-I-Y-G-E-F-E-A-K-K-K-K-CONH$_2$, wherein Ja133 is LightCycler-Red 640-N-hydroxy succinimide ester;

whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of amino acids each protected by temporary piperidine labile Fmoc- and permanent acid labile tert-Bu-, BOC— and Otert-Bu-groups depending on the side chain function. The substrate sequence AEEE-IYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased by Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoracetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].

Enzymes: Upstate Lck (p56$^{lck}$, active), Upstate Src (p60$^{c-src}$, partially purified) were purchased from UBI.

Time-resolved Fluorescence Assay: Reader: Perkin Elmer, Wallac Viktor 1420-040 multilabel counter; Liquid handling system: Beckman Coulter, Biomek 2000. ATP, Tween 20, HEPES were purchased from Roche Molecular Biochemicals, MgCl$_2$ and MnCl$_2$ were purchased from Merck Eurolab, TCEP was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The IC50-values can be obtained from the reaction rates by using a non-linear curve fit (Excelfit).

| Example No. | Compound Name | IC 50 (src) [nM] | IC 50 (lck) [nM] |
|---|---|---|---|
| 13-3 | 3-(2-bromo-phenyl)-1-methyl-7-(2-methyl-2,3-dihydro-1H-isoindol-5-ylamino)-3,4-dihydro-1H-pyrimido[4,5-d]pyrimidin-2-one; hydrochloride salt | 1.5 | 4.2 |
| 13-4 | 3-(2-bromo-phenyl)-7-(3,3-dioxo-2,3-dihydro-3lambda*6*-benzo[1,3]oxathiol-5-ylamino)-1-methyl-3,4-dihydro-1H-pyrimido[4,5-d]pyrimidin-2-one | 17 | 29.4 |
| 13-8 | 7-(benzo[1,3]dioxol-5-ylamino)-3-(2-bromo-phenyl)-1-methyl-3,4-dihydro-1H-pyrimido[4,5-d]pyrimidin-2-one | 17 | 20 |
| 1 | 3-(2-bromo-phenyl)-7-(2-hydroxymethyl-2,3-dihydro-benzo[1,4]dioxin-6-yino)-1-methyl-3,4-dihydro-1H-pyrimido[4,5-d]pyrimidin-2-one | 7.5 | 6.3 |
| 13-12 | 3-(2-bromo-6-fluoro-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one | 4.2 | 14 |
| 13-16 | 5-[6-(2-bromo-6-fluoro-phenyl)-8-methyl-7-oxo-5,6,7,8-tetrahydro-pyrimido[4,5-d]pyrimidin-2-ylamino]-2-methyl-isoindole-1,3-dione | 11 | 21 |
| 8 | 3-(2-bromo-6-fluoro-phenyl)-7-(4,4-dioxo-3,4-dihydro-2H-4lambda*6*-benzo [1,4]oxathiin-6-ylamino)-1-methyl-3,4-dihydro-1H-pyrimido[4,5-d]pyrimidin-2-one | 1.8 | 4.7 |
| 11 | 3-(2-bromo-6-fluoro-phenyl)-1-methyl-7-(4-methyl-1,1-dioxo-1,2,3,4-tetrahydro-1lambda*6*-benzo[1,4]thiazin-7-ylamino)-3,4-dihydro-1H-pyrimido[4,5-d]pyrimidin-2-one | 0.8 | 4.3 |
| 13-29 | 3-(2-bromo-6-fluoro-phenyl)-1-methyl-7-(4-methyl-1,1,3-trioxo-1,2,3,4-tetrahydro-1lambda*6*-benzo[1,4]thiazin-7-ylamino)-3,4-dihydro-1H-pyrimido[4,5-d]pyrimidin-2-one | 2.5 | 6.7 |
| 7 | 3-(2-bromo-phenyl)-3,4-dihydro-7-(-spiro[1,3-benzodioxolo-2,4'-piperidine]-5-yl)amino-1-methyl-pyrimido[4,5-d]pyrimidin-2(1H)-one | 2.0 | 2.4 |

-continued

| Example No. | Compound Name | IC 50 (src) [nM] | IC 50 (lck) [nM] |
|---|---|---|---|
| 13-46 | 3-(2-bromo-6-fluoro-phenyl)-3,4-dihydro-7-(spiro[1,3-benzodioxolo-2,4'-piperidine]-5-yl)amino-1-methyl-pyrimido[4,5-d]pyrimidin-2(1H)-one | 2.3 | 2.6 |
| 13-48 | 3-(2-Bromo-5-methoxy-phenyl)-7-(4,4-dioxo-3,4-dihydro-2H-4lambda*6*-benzo[1,4]oxathiin-6-ylamino)-1-methyl-3,4-dihydro-1H-pyrimido[4,5-d]pyrimidin-2-one | 72.8 | 37.5 |
| 13-49 | 7-(4,4-Dioxo-3,3-dihydro-2H-4lambda*6*-benzo[1,4]oxathiin-6-ylamino)-3-(2-fluoro-6-methoxy-phenyl)-1-methyl-3,4-dihydro-1H-pyrimido[4,5-d]pyrimidin-2-one | 7.2 | 5.4 |
| 8a | 3-(2-Bromo-phenyl)-7-(4,4-dioxo-3,4-dihydro-2H-4lambda*6*-benzo[1,4]oxathiin-6-ylamino)-1,4-dimethyl-3,4-dihydro-1H-pyrimido[4,5-d]pyrimidin-2-one; enantiomer 1 | 0.4 | 8.1 |
| 13-50 | 3-(2-Bromo-phenyl)-7-(4,4-dioxo-3,4-dihydro-2H-4lambda*6*-benzo[1,4]oxathiin-6-ylamino)-1,4-dimethyl-3,4-dihydro-1H-pyrimido[4,5-d]pyrimidin-2-one; enantiomer 2 | 2965.8 | 1342.4 |
| 13-51 | 3-(2-Bromo-phenyl)-1,4-dimethyl-7-(4-methyl-1,1,3-trioxo-1,2,3,4-tetrahydro-1lambda*6*-benzo[1,4]thiazin-7-ylamino)-3,4-dihydro-1H-pyrimido[4,5-d]pyrimidin-2-one; enantiomer 2 | 2521.6 | 1280.4 |
| 13-52 | 3-(2-Bromo-phenyl)-1,4-dimethyl-7-(4-methyl-1,1,3-trioxo-1,2,3,4-tetrahydro-1lambda*6*-benzo[1,4]thiazin-7-ylamino)-3,4-dihydro-1H-pyrimido[4,5-d]pyrimidin-2-one; enantiomer 1 | 0.019 | 0.0246 |
| 13-53 | 2-[7-(4,4-Dioxo-3,4-dihydro-2H-4lambda*6*-benzo[1,4]oxathiin-6-ylamino)-1-methyl-2-oxo-1,4-dihydro-2H-pyrimido[4,5-d]pyrimidin-3-yl]-3-fluoro-benzonitrile | 4.3 | 12.9 |

Pharmakokinetic Studies:

The improved pharmacokinetics of the compounds according to this invention was demonstrated according to the following procedure:

To male NMRI mice of 29–35 g body weight the compounds according to this invention were given p.o. as micro-suspensions (7.5% modified gelatine and 0.22% NaCl) in doses of 30 mg/kg (Drug concentration: 3 mg/mL. Administered volume: 10 mL/kg) and as single dose administration.

Study Protocol:

Animals were fasted overnight up to 4 hrs. after administration of the compound. For each single p.o. dose the mice were allocated to 3 groups with 4 animals each. Blood samples are taken from group 1 at 0.5, 3 and 24 hours, from group 2 at 1 and 6 hours, and from group 3 at 2 and 8 hours.

Blood samples of about 200 µl were obtained by retro-orbital puncture. Plasma samples were obtained from heparinized/EDTA blood by centrifugation at room temperature, and stored frozen at −20° C. until analysis.

Analysis:

Plasma was deproteinated and subsequently analysed for plasma levels of the compound by a compound specific HPLC-MS method. WinNonlin™ was used to calculate the pharmacokinetic parameters.

Results:

| Example No | Compound names | AUC = area under the curve from T = 0 to T = 24 hrs [(h * ng/ ml))/ (mg/kg)] |
|---|---|---|
| Reference cpd 43 from WO 00/24744A | 3-(2-bromo-phenyl)-7-[4-(2-diethylamino-ethoxy)-phenylamino]-1-methyl-3,4-dihydro-1H-pyrimido[4,5-d]pyrimidin-2-one | 69.3 |
| 6 | 3-(2-bromo-phenyl)-3,4-dihydro-7-(1'-acetyl-spiro[1,3-benzodioxolo-2,4'-piperidine]- 5-yl)amino-1-methyl-pyrimido[4,5-d]pyrimidin-2(1H)-one | 315 |
| 1 | 3-(2-bromo-phenyl)-7-(2-hydroxymethyl-2,3-dihydro benzo[1,4]dioxin-6-ylamino)-1-methyl-3,4-dihydro-1H-pyrimido[4,5-d]pyrimidin-2-one | 379 |
| 7 | 3-(2-bromo-phenyl)-3,4-dihydro-7-(-spiro[1,3-benzodioxolo-2,4'-piperidine]-5-yl)amino-1-methyl-pyrimido[4,5-d]pyrimidin-2(1H)-one | 813 |

-continued

| Example No | Compound names | AUC = area under the curve from T = 0 to T = 24 hrs [(h * ng/ml))/(mg/kg)] |
|---|---|---|
| 13-46 | 3-(2-bromo-6-fluoro-phenyl)-3,4-dihydro-7-(spiro[1,3-benzodioxolo-2,4'-piperidine]-5-yl) amino-1-methyl-pyrimido[4,5-d]pyrimidin-2(1H)-one | 234 |
| 13-21 | 3-(2-bromo-phenyl)-1-methyl-7-(2-pyrrolidin-1-ylmethyl-2,3-dihydro-benzo[1,4]dioxin-6-ylamino)-3,4-dihydro-1H-pyrimido[4,5-d]pyrimidin-2-one | 120 |
| 13-12 | 3-(2-bromo-6-fluoro-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one | 592 |

The invention is further illustrated by the following, non-limiting preparation examples, wherein the following abbreviations are used:
TCL thin layer chromatography
HPLC high performance liquid chromatogrphy
MS mass spectroscopy
TFA trifluoroacetic acid
NMP N-methylpyrrolidone
DMF N,N-dimethylformamide
THF tetrahydrofurane
mCPBA m-chloro-perbenzoic acid
LAH lithium aluminium hydride

PREPARATION EXAMPLES

Starting Materials:

a) 2-Hydroxymethyl-6-nitro-1,4-benzodioxane 1.93 g 60% sodium hydride were washed with hexanes and suspended in 90 ml DMF. At 5° C. a solution of 5.15 g 4-nitrobrenzcatechol in 30 ml DMF was added dropwise in 15 min. Subsequently, 5.00 g epibromohydrine in 10 ml DMF were added over 15 min. Stirring was continued for 30 min at room temperature, then at 80° C. for another 3 hrs. The mixture was poured in portions into ice water and extracted with diethyl ether. The organic phase was dried and evaporated and the residue recrystallized from toluene. The first crop of crystals (2.78 g) was suspended in 20 ml MeOH at room temperature, filtered and the filtrate evaporated to give 1.65 g of the title product.

Additional 0.5 g of a second crop were obtained from the toluene mother liquor.

b) 2-Hydroxymethyl-6-amino-1,4-benzodioxane 4.2 g of the above nitro compound in 120 ml MeOH were hydrogenated at atmospheric pressure with 10% Pd—C at room temperature for 3 hrs. The mixture was filtered and the filtrate evaporated to yield 3.13 g of the title compound.

c) 1'-Acetyl-5-nitro-spiro[1,3-benzodioxolo-2,4'-piperidine]

156 g 65% nitric acid were mixed with 40 ml acetic acid with cooling. 19.8 g 1'-Acetyl-spiro[1,3-benzodioxolo-2,4'-piperidine] in 60 ml acetic acid were added at 4–8° C. within 50 min. The mixture was stirred at 5° C. for 1.5 hrs, then poured into ice water and extracted with ethyl acetate. The combined organic phases were washed with aqueous sodium bicarbonate and evaporated to yield 17.5 g of the title product.

d) 5-Amino-1'-acetyl-spiro[1,3-benzodioxolo-2,4'-piperidine]

The above nitro compound was hydrogenated with Pd—C in THF at ambient pressure and temperature for 5 hrs. Filtration and evaporation of the filtrate yielded 12.35 g of the title compound.

e) 5-Amino-spiro[1,3-benzodioxolo-2,4'-piperidine]

5 g 5-Amino-1'-acetyl-spiro[1,3-benzodioxolo-2,4'-piperidine] (from d)) and 5.317 g potassium hydroxide were refluxed in a mixture of 30 ml ethanol and 10 ml water for 18 hrs. After cooling to room temperature, the mixture solidified and was diluted by 20 ml water and extracted three times with CH2Cl2. The combined organic phases were dried and evaporated to yield 3.45 g of the title compound.

f) 5-Amino-1'-(2-methoxyethyl)-spiro[1,3-benzodioxolo-2,4'-piperidine]

1.134 g of the above compound was suspended in 30 ml THF and 0.782 g ethyldiisopropyl amine were added. 0.764 g 2-methoxybromoethane in 3 ml THF were added dropwise at 10° C. and stirring continued at room temperature for 3.5 hrs, then the mixture was heated to 50° C. for 68 hrs. 3 ml conc. Aqueous sodium bicarbonate were added and the THF was evaporated. The residue was diluted by another 10 ml water and the product extracted with $CH_2Cl_2$ and purified by chromatography on silica (CHCl3/MeOH 95/5).

Yield: 0.543 g of the title compound.

g) 6-Nitro-2,3-dihydro-benzo[1,4]oxathiine-4,4-dioxide 2.554 g 66% H2SO4 and 1.454 g 65% nitric acid were mixed at 0° C. 2.395 g 2,3-dihydro-benzo[1,4]oxathiine-4,4-dioxide were added in portions at 0° C. After stirring for 30 min. the mixture was diluted with water and the product isolated by filtration. Chromatography on silica yielded 1.6 g of the title compound and 0.37 g 0.58 g of the 8-nitro isomer.

h) 6-Amino-2,3-dihydro-benzo[1,4]oxathiine-4,4-dioxide 0.917 g 6-Nitro-2,3-dihydro-benzo[1,4]oxathiine-4,4-dioxide (from g)) were hydrogenated in a mixture of 20 ml THF and 20 ml MeOH with 0.90 g 5% Pd—C at atmospheric hydrogen pressure for 90 min. at room temperature. The catalyst was filtered off, the filtrate evaporated and the residue chromatographed on silica to yield 370 mg of the title compound.

i) 6-Amino-4-methyl-4H-benzo[1,4]thiazin-3-one 4.5 g 6-Amino-4H-benzo[1,4]thiazin-3-one in 50 ml DMF was treated in portions with 0.695 g 95% sodium hydride at room temperature. After 30 min, 3.548 g methyl iodide were added dropwise at 0° C. and stirring was continued for another 30 min. The mixture was poured into ice and ammonium chloride solution and extracted with $CH_2Cl_2$. Chromatography on silica yielded 3.1 g crude product, which was further purified by trituration with diethyl ether.

Yield: 3.00 g of the title compound.

j) 7-Nitro-4-methyl-4H-benzo[1,4]thiazin-3-one 7.3 g 7-Nitro-4H-benzo[1,4]thiazin-3-one was suspended in 65 ml DMF and treated in portions with 1.6 g of 55% sodium hydride. Stirring a room temperature was continued for 0.5 hrs, than 5.2 g methyl iodide in 15 ml DMF were added dropwise. After another 3 hrs the mixture was poured into ice water and the title product isolated by filtration in a yield of 7.5 g.

k) 7-Amino-4-methyl-4H-benzo[1,4]thiazin-3-one 3.7 g of the above nitro compound was hydrogenated in THF over 10% Pd—C at room temperature. Filtration and evaporation of the solvent gave 3.07 g of the title product.

l) 7-Nitro-4-methyl-4H-benzo[1,4]thiazine 7 g 7-Nitro-4-methyl-4H-benzo[1,4]thiazin-3-one (from j)) in 10 ml THF were treated dropwise with 67.57 ml 2M borane dimethyl sulfide complex in THF at room temperature. After 16 hrs the mixture was poured into saturated aqueous sodium bicarbonate and extracted with ethyl acetate. The solvent was evaporated and the solid residue triturated with ether.

Yield: 5.80 g of the title compound.

m) 7-Nitro-4-methyl-4H-benzo[1,4]thiazin-1,1-dioxide

To 3 g 7-Nitro-4-methyl-4H-benzo[1,4]thiazine (from 1)) in 70 ml $CH_2Cl_2$ were added dropwise a solution of 8.62 g 60% mCPBA in 100 ml $CH_2Cl_2$, dried over sodium sulfate. After stirring for 16 hrs at room temperature the mixture was washed with aqueous sodium sulfite and sodium carbonate, then evaporated and chromatographed on silica.

Yield: 2.55 g of the title compound and 0.34 g of the corresponding sulfoxide.

n) 7-Amino-4-methyl-4H-benzo[1,4]thiazin-1,1-dioxide 2.4 g of the above nitro compound was hydrogenated as in ex. k and purified by chromatography on silica.

Yield: 1.15 g of the tide compound o) 7-Nitro-4-methyl-4H-benzo[1,4]thiazin-3-one-1,1-dioxide 2 g 7-Nitro-4-methyl-4H-benzo[1,4]thiazin-3-one (from j)) in 30 ml $CH_2Cl_2$ were treated with a dried solution of 5.387 g 60% mCPBA in 150 ml $CH_2Cl_2$ at room temperature. After stirring for 16 hrs, the mixture was washed with aqueous sodium sulfite and sodium carbonate, dried and evaporated. The residue was triturated with ether.

Yield: 2.18 g of the title compound.

p) 7-Amino-4-methyl-4H-benzo[1,4]thiazin-3-one-1,1-dioxide 1.5 g of the above nitro compound were hydrogenated over 3 g 10% Pd—C in 70 ml THF at atmospheric pressure. After 2 hrs. the mixture was filtered and the filtrate evaporated. The solid residue was triturated with ether.

Yield: 1.03 g of the title compound.

q) 2-Methyl-2,3-dihydro-1H-isoindol-5-ylamine 2.643 g 4-Amino-N-methylphthalimide was suspended in 50 ml THF and added to 1.328 g lithium aluminum hydride in 50 ml THF at room temperature. The mixture was refluxed for 3 hrs, then stirred a further 3 days at room temperature. Excess LAH was destroyed by addition of water and the mixture filtered over celite. An aqueous phase was separated and extracted with $CH_2Cl_2$. The combined organic phases were dried and evaporated. The residue was stirred with HCl in MeOH and the evaporated to yield 1.6 g of the title compound as the hydrochlorid salt.

r) 2-(1,1-dimethyl-2-hydroxyethyl)-5-nitro-2,3-dihydro-1H-isoindol 20 g of 4-Nitro-phthalic anhydride and 8.94 g of 2-amino-2-methylpropanol were heated to 170° C. for 30 min. After cooling, water and CH2Cl2 were added, and the organic phase separated, concentrated and purified by chromatography on silica (eluent CH2Cl2/MeOH 97/3).

s) 2-(1,1-dimethyl-2-hydroxyethyl)-2,3-dihydro-1H-isoindol-5-ylamine 1.1 g of the above nitro-compound were hydrogenated in 130 ml THF with 2.2 g Pd on charcoal (10%) at room temperature and atmospheric pressure. After 2.5 hrs the mixture was filtered and the filtrate evaporated to give 0.78 g of the title compound.

t) 1-(4-Methylamino-2-methylsulfanyl-pyrimidin-5-yl)-ethanol 1.5 g 4-Methylamino-2-methylsulfanyl-pyrimidine-5-carbaldehyde were dissolved in 30 ml THF and 14 ml of a 1.4 M solution of methyl magnesium bromide in ether were added dropwise below 5° C. After stirring for 1 hr at 0° C., another 14 ml Grignard solution were added within 30 min. Stirring was continued for 30 min at 0° C. and finally at RT for 25 hrs. The mixture was quenched with saturated ammonium chloride solution and extracted with ethyl acetate.

Yield: 1.57 g of crude title product.

u) [5-(1-Chloro-ethyl)-2-methylsulfanyl-pyrimidin-4-yl]-methyl-amine 0.25 g of the product from example t) were dissolved in 10 ml chloroform and 0.30 g thionyl chloride were added dropwise. The mixture was refluxed for 2 hrs and evaporated to yield 0.31 g of the title product as the hydrochloride salt.

v) 5-[1-(2-Bromo-phenylamino)-ethyl]-2-methylsulfanyl-pyrimidin-4-ylmethyl-amine 0.25 g of the product from example u) and 34 mg sodium iodide in 10 ml acetonitrile were stirred for 15 min at RT. The resulting suspension was added dropwise at RT to a mixture of 0.21 g 2-bromoanilin and 0.33 g N-ethyl-diisopropyl amine in 5 ml acetonitrile. Stirring was continued for 16 hrs and the mixture was diluted with 20 ml water and extracted with dichloromethane. Chromatography on silica (eluent CHCl3) yielded 158 mg of the title product.

w) 2-[(4-Methylamino-2-methylsulfanyl-pyrimidin-5-ylmethyl)-amino]benzonitrile

Analogous to example v) 0.4 g of the title product can be obtained from 1.0 g (5-chloromethyl-2-methylsulfanyl-pyrimidin-4-yl)-methyl-amine hydrochloride and 0.527 g 2-cyano-anilin.

x) 2-Hydroxymethyl-7-nitro-1,4-benzodioxane 17.6 g 4-nitrocatechol and 11.0 g potassium bicarbonate were stirred in 200 ml DMF at 10° C. 13.99 g epibromohydrin in 10 ml DMF were added dropwise and stirring was continued at 60° C. for another 17 hrs. DMF was evaporated and the residue diluted with 50 ml water and extracted with ethyl acetate. The combined organic phases were washed with caustic soda and water., dried and evaporated. The crude oily product was heated to 90° C. with 200 ml toluene and the supernatant decanted from insoluble parts. After cooling to RT the solution is again decanted from insoluble oils and left at RT for 3 d. A first crop of 0.75 g crystalline title product was obtained. The mother liquor was evaporated and the residue dissolved in 20 dichloromethane at RT. Seeding and chilling to 0° C. yielded another 2.78 g crystalline title product.

y) 2-Chloromethyl-7-nitro-1,4-benzodioxane 3.5 g of the product from example x) in 50 ml toluene were treated with 2.06 g thionyl chloride in 4 ml toluene and refluxed for 1.5 hrs. Another 0.5 g thionyl chloride were added and reflux continued for 7 hrs. Further 0.5 g thionyl chloride were added and reflux continued for another 9 hrs. After cooling to RT, 1.6 ml pyridine were added and the mixture heated to 60–70° C. for 16 hrs. with TLC control.

Another 0.2 ml pyridine were added and heating continued for another 4 hrs. Finally, the mixture was washed with water and sodium carbonate solution, dried and evaporated to yield 3.05 g of the crude title product, which was used in subsequent reactions without further purification.

z) 4-(7-Nitro-2,3-dihydro-benzo[1,4]dioxin-2-ylmethyl)-morpholine 0.80 g of the chloromethyl compound from example x), 0.61 g morpholine and 50 mg sodium iodide in 2.5 ml NMP were heated to 100° C. for 21 hrs. The mixture was diluted with 10 ml water and 1 ml saturated sodium carbonate solution and extracted with ethyl acetate. Chromatography of the crude product on silica yielded 0.67 mg of the title product.

za) 3-(2-Bromo-phenyl)-1,4-dimethyl-7-methylsulfanyl-3,4-dihydro-1H-pyrimido[4,5-d]pyrimidin-2-one; enantiomers 1+2

To 1.1 g of the product from example v) in 10 ml dry DMF were added 0.236 sodium hydride (95%) with cooling. After stirring for 20 min at RT, the mixture was cooled to 5 C and treated in small portions with a total of 1.01 g carbonyldiimidazole. Stirring was continued at 5 C for 30 min and at RT over night. Excess sodium hydride was then destroyed by addition of a small amount of water under cooling. The mixture was diluted with water, extracted with ethyl acetate and the combined organic phases evaporated.

The crude product was chromatographed on a chiral phase Chiracel OD-CSP (commercial 20 μm material from Daicel, eluent heptane/iso-propanol 1:1) to yield 470 mg of each of the two separated enantiomers of the title product as pale yellow powders. The first and second eluting enantiomer is termed 'enantiomer 1' and 'enantiomer 2' respectively. Likewise the corresponding enantiomer of a chiral final product derived from one of the two enantiomeric starting materials is also termed 'enantiomer 1' or 'enantiomer 2' respectively.

zb) 3-(2-Bromo-phenyl)-7-methanesulfonyl-1,4-dimethyl-3,4-dihydro-1H-pyrimido[4,5-d]pyrimidin-2-one; enantiomer 1

0.628 g commercial meta-chloroperbenzoic acid (77%) were dissolved in 50 ml CH2Cl2 and this solution was dried by filtration over sodium sulfate. The dried MCPBA solution was added to a solution of 0.437 g of the enantiomer 1 from example za) in 20 ml CH2Cl2 dropwise at RT and stirring was continued over night. Excess peracid was destroyed by washing with dilute sodium bisulfite solution. The organic phase was washed with aqueous sodium bicarbonate, dried, and evaporated. Chromatography over silica in ethyl acetate/heptane yielded 430 mg of the title product.

Final Products

Example 1

3-(2-bromo-phenyl)-7-(2-hydroxymethyl-2,3-dihydro-benzo[1,4]dioxin-6-ylamino)-1-methyl-3,4-dihydro-1H-pyrimido[4,5-d]pyrimidin-2-one 1.2 g 3-(2-bromo-phenyl)-3,4-dihydro-7-methanesulphonyl-1-methyl-pyrimido[4,5-d]pyrimidin-2(1H)-one and 1.54 g 2 hydroxymethyl-6-amino-1,4-benzodioxane (starting material b)) were mixed in 20 ml NMP. 0.348 g TFA were added and the mixture was heated to 140° C. for 7 hrs. The mixture was poured into 10% aqueous HCl and extracted with ethyl acetate. The aqueous phase was adjusted to pH>9 and extracted with $CH_2Cl_2$. The organic phases were combined and evaporated. The residue was suspended in $CH_2Cl_2$ at room temperature and solid impurities were filtered off. The filtrate was washed again with water to remove remainders of NMP, then evaporated. The residue was triturated with water, filtered and dried to give 0.6 g of the title product (mp: 156–158° C.). NMR (CDCl3, δ in ppm): 2.03 (broad s, 1 H); 3.48 (s, 3H); 3.89 (dd, 1H); 3.95 (dd, 1H); 4.15 (dd, 1H); 4.28 (m, 1H); 4.33 (dd, 1H); 4.55 (d, 1H); 4.71 (d, 1H); 6.89 (m, 1H); 6.98 (m, 2H); 7.25 (m, 1H); 7.40 (m, 3H); 7.71 (d, 1H); 7.98 (s, 1H). MS (APCI$^+$): 498 (M+1), 420 (M-Br)

Example 2

3-(2-bromo-phenyl)-3,4-dihydro-7-(2-chloromethyl-benzodioxane-6-yl)amino-1-methyl-pyrimido[4,5-d]pyrimidin-2 (1H)-one 170 mg of the product from example 1 were suspended in 20 ml toluene. At 100° C. 45 mg thionylchloride were added and the mixture heated to reflux. After a few hrs TLC and HPLC indicated complete conversion and the solvent was distilled off at 90° C. by applying slight vacuum. The chloromethyl derivative thus obtained was used without further purification.

Example 3

3-(2-bromo-phenyl)-1-methyl-7-(2-morpholin-4-ylmethyl-2,3-dihydro-benzo[1,4]dioxin-6-ylamino)-3,4-dihydro-1H-pyrimido[4,5-d]pyrimidin-2-one 85 mg of the chloromethyl compound from example 2 and 130 mg morpholine were mixed in 8 ml NMP. 24 mg tetrabutyl ammonium bromide were added and the mixture was heated to 50° C. for 18 hrs. Another 24 mg tetrabutyl ammonium bromide were added and the temperature was raised to 100° C. for 16 hrs, then to 130° C. for another 6 hrs. Separation of the crude mixture by HPLC-MS yielded 40 mg of the title compound.

Example 4

3-(2-bromo-phenyl)-3,4-dihydro-7-[2-(p-toluene-sulfonyl)oxymethyl-benzodioxane-6-yl]amino-1-methyl-pyrimido[4,5-d]pyrimidin-2(1H)-one 520 mg of the product from example 1 were dissolved in 20 ml CHCl3. 213 mg tosyl chloride and 13 mg 4-dimethylaminopyridine were added and the mixture was cooled to 5° C. 166 mg pyridine were added dropwise and stirring was continued at room temperature for 3 hrs. The mixture was stirred 1 hr at 60° C., then another 105 mg tosyl chloride were added and stirring was continued at room temperature for 16 hrs. The mixture was diluted with 50 ml CHCl3 and washed with 0.5 M HCl, dried and evaporated. Chromatography on silica yielded 180 mg of the title compound.

Example 5

3-(2-bromo-phenyl)-7-(2-dimethylaminomethyl-2,3-dihydro-benzo[1,4]dioxin-6-ylamino)-1-methyl-3,4-dihydro-1H-pyrimido[4,5-d]pyrimidin-2-one 90 mg of the tosylate from example 4 in 8 ml NMP were treated with 0.62 ml 2 M dimethylamine in THF and stirred at room temperature for 3 d. The mixture was heated to 50°

C. for 4 hrs, then to 65° C. for another 2 hrs. Stirring was continued at 45° C. over night. Separation by HPLC-MS yielded crude product contaminated by NMP, which was further purified by dissolving in CHCl3 and washing with water.

Yield: 27 mg of the title compound.

Example 6

3-(2-bromo-phenyl)-3,4-dihydro-7-(1'-acetyl-spiro [1,3-benzodioxolo-2,4'-piperidine]-5-yl)amino-1-methyl-pyrimido[4,5-d]pyrimidin-2(1H)-one 80 mg 3-(2-bromo-phenyl)-3,4-dihydro-7-methane-sulphonyl-1-methyl-pyrimido-[4,5-d]pyrimidin-2(1H)-one and 207 mg 5-Amino-1'-acetyl-spiro[1,3-benzodioxolo-2,4'-piperidine] (starting material d)) in 0.8 ml NMP were treated with 23 mg TFA and heated to 140° C. under N2 for 15 hrs. Purification by preparative HPLC-MS, followed by dissolving in ethyl acetate and washing with dilute aqueous HCl, yielded 57 mg of the title compound (mp: 200–201° C.).

Example 7

3-(2-bromo-phenyl)-3,4-dihydro-7-(spiro[1,3-benzo-dioxolo-2,4'-piperidine]-5-yl)amino-1-methyl-pyrimido[4,5-d]pyrimidin-2(1H)-one 82 mg 5-Amino-spiro[1,3-benzodioxolo-2,4'-piperidine] (starting material e)) in 2 ml THF were added to 0.4 ml of a 1M solution of lithium hexamethyldisilazide in THF at 0° C. and stirred for 20 min. 89 mg 3-(2-bromo-phenyl)-3,4-dihydro-7-methanesufphonyl-1-methyl-pyrimido[4,5-d]pyrimidin-2(1H)-one were added as a suspension in 2 ml THF at 0° C. and stirring was continued at room temperature for 16 hrs. The mixture was poured into water and extracted with ethyl acetate. The organic phase was concentrated and purified by preparative HPLC-MS. Product containing fractions were dissolved in CH$_2$Cl$_2$ and washed with aqueous sodium hydroxide, then dried and evaporated.

Yield: 5 mg of the title compound (mp: 229–231° C.).

Example 8

3-(2-bromo-6-fluoro-phenyl)-7-(4,4-dioxo-3,4-dihydro-2H-4λ$^6$-benzo[1,4]oxathiin-6-ylamino)-1-methyl-3,4-dihydro-1H-pyrimido[4,5-d]pyrimidin-2-one 83 mg 3-(2-bromo-6-fluorophenyl)-3,4-dihydro-7-methanesulphonyl-1-methyl-pyrimido[4,5-d]pyrimidin-2(1H)-one and 80 mg 6-Amino-2,3-dihydro-benzo[1,4]oxathiine-4,4-dioxide (starting material h)) in 0.8 ml NMP were treated with 0.2 ml 2M HCl in ether and heated to 120° C. for 6 hrs. From this mixture 21 mg of the title product were isolated by preparative HPLC-MS (mp: 230–233° C.).

Example 8a 3-(2-Bromo-phenyl)-7-(4,4-dioxo-3,4-dihydro-2H-4λ$^6$-benzo[1,4]oxathiin-6-ylamino)-1,4-dimethyl-3,4-dihydro-1H-pyrimido[4,5-d]pyrimidin-2-one; enantiomer 1

Analogous to the procedure of example 8, but using 100 mg of the product from example zb) and 145 mg of starting material h) the title compound can be obtained as a pale yellow powder.

Yield: 25 mg of the title compound.

Example 9

3-(2-bromo-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one 320 mg 3-(2-bromo-phenyl)-3,4-dihydro-7-methane-sulphonyl-1-methylpyrimido-[4,5-d]pyrimidin-2(1H)-one and 626 mg 7-amino-4-methyl-4H-benzo[1,4]thiazin-3-one (starting material k)) in 4 ml NMP were treated with 92 mg TFA and heated to 140° C. for 12 hrs. The mixture was diluted with aqueous HCl and the precipitated product collected by filtration.

Yield: 245 mg of the title compound.

Example 10

3-(2-Bromo-phenyl)-7-(3-methoxy-4-methyl-1-oxo-1,4-dihydro-1lambda*4*-benzo[1,4]thiazin-7-ylamino)-1-methyl-3,4-dihydro-1H-pyrimido[4,5-d] pyrimidin-2-one 100 mg of the compound from example 9 and 108 mg oxone were stirred in 2 ml MeOH at room temperature for 17 hrs. The mixture was filtered and the residue washed with THF. The combined filtrates were concentrated and purified by preparative HPLC-MS to yield 10 mg of the title compound.

Example 11

3-(2-bromo-6-fluoro-phenyl)-1-methyl-7-(4-methyl-1,1-dioxo-1,2,3,4-tetrahydro-1lambda*6*-benzo[1,4]thiazin-7-ylamino)-3,4-dihydro-1H-pyrimido[4,5-d]pyrimidin-2-one 83 mg 3-(2-bromo-6-fluorophenyl)-3,4-dihydro-7-methanesulphonyl-1-methyl-pyrimido[4,5-d]pyrimidin-2(1H)-one and 85 mg 7-Amino-4-methyl-4H-benzo[1,4]thiazin-1,1-dioxide (starting material n)) in 0.8 ml NMP were treated with 0.2 ml 2M HCl in ether and heated to 120° C. for 6 hrs. The mixture was purified by preparative HPLC-MS to yield 34 mg of the title compound.

Example 12

3-(2-Bromo-6-fluoro-phenyl)-7-[2-(2-hydroxy-1,1-dimethyl-ethyl)-2,3-dihydro-1H-isoindol-5-ylamino]-1-methyl-3,4-dihydro-1H-pyrimido[4,5-d]pyrimidin-2-one; hydrochloride 80 mg 3-(2-bromo-6-fluorophenyl)-3,4-dihydro-7-methanesulphonyl-1-methyl-pyrimido[4,5-d]pyrimidin-2(1H)-one and 82 mg 2-(1,1-dimethyl-2-hydroxyethyl)-2,3-dihydro-1H-isoindol-5-ylamine (starting material s)) were mixed in 1 ml dry NMP. 0.2 ml 2M HCl in ether were added and the mixture heated to 120° C. for 24 hrs under N2 atmosphere. The product was isolated from the mixture by preparative HPLC-MS and further purified by a second chromatography on silica. The pure fractions were dissolved in CH$_2$Cl$_2$ and treated with one equivalent of 2M HCl in ether. Evaporation yielded 1.5 mg of the hydrochloride salt of the title product.

Example 13

The following additional compounds were obtained according to the preparation methods and examples described hereinbefore:

Example 13-1

3-(2-bromo-phenyl)-1-methyl-7-(3-oxo-3,4-dihydro-2H-benzo[1,4]thiazin-7-ylamino)-3,4-dihydro-1H-pyrimido[4,5-d]pyrimidin-2-one,

Example 13-2

5-[6-(2-bromo-phenyl)-8-methyl-7-oxo-5,6,7,8-tetrahydro-pyrimido[4,5-d]pyrimidin-2-ylamino]-2-methyl-isoindole-1,3-dione,

Example 13-3

3-(2-bromo-phenyl)-1-methyl-7-(2-methyl-2,3-dihydro-1H-isoindol-5-ylamino)-3,4-dihydro-1H-pyrimido[4,5-d]pyrimidin-2-one; hydrochloride salt,

Example 13-4

3-(2-bromo-phenyl)-7-(3,3-dioxo-2,3-dihydro-3lambda*6*-benzo[1,3]oxathiol-5-ylamino)-1-methyl-3,4-dihydro-1H-pyrimido[4,5-d]pyrimidin-2-one,

Example 13-5

3-(2-bromo-phenyl)-1-methyl-7-(4-methyl-1,3-dioxo-1,2,3,4-tetrahydro-1$\lambda^4$-benzo[1,4]thiazin-7-ylamino)-3,4-dihydro-1H-pyrimido[4,5-d]pyrimidin-2-one

Example 13-6

3-(2-bromo-phenyl)-1-methyl-7-(4-methyl-3,4-dihydro-2H-benzo[1,4]thiazin-7-ylamino)-3,4-dihydro-1H-pyrimido[4,5-d]pyrimidin-2-one,

Example 13-7

3-(2-bromo-phenyl)-1-methyl-7-(3-oxo-3,4-dihydro-2H-benzo[1,4]thiazin-6-ylamino)-3,4-dihydro-1H-pyrimido[4,5-d]pyrimidin-2-one,

Example 13-8

7-(benzo[1,3]dioxol-5-ylamino)-3-(2-bromo-phenyl)-1-methyl-3,4-dihydro-1H-pyrimido[4,5-d]pyrimidin-2-one,

Example 13-9

3-(2-bromo-phenyl)-7-(2,3-dihydro-benzo[1,4]dioxin-6-ylamino)-1-methyl-3,4-dihydro-1H-pyrimido[4,5-d]pyrimidin-2-one,

Example 13-10

3-(2-bromo-phenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one,

Example 13-11

5-[6-(2-bromo-phenyl)-8-methyl-7-oxo-5,6,7,8-tetrahydro-pyrimido[4,5-d]pyrimidin-2-ylamino]-isoindole-1,3-dione,

Example 13-12

3-(2-bromo-6-fluoro-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one (mp: 145–149° C.),

Example 13-13

3-(2-bromo-6-fluoro-phenyl)-1-methyl-7-(3-oxo-3,4-dihydro-2H-benzo[1,4]thiazin-6-ylamino)-3,4-dihydro-1H-pyrimido[4,5-d]pyrimidin-2-one,

Example 13-14

3-(2-bromo-6-fluorophenyl)-3,4-dihydro-7-(1'-acetyl-spiro[1,3-benzodioxolo-2,4'-piperidine]-5-yl)amino-1-methyl-pyrimido[4,5-d]pyrimidin-2(1H)-one,

Example 13-15

3-(2-bromo-6-fluorophenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one,

Example 13-16

5-[6-(2-bromo-6-fluoro-phenyl)-8-methyl-7-oxo-5,6,7,8-tetrahydro-pyrimido[4,5-d]pyrimidin-2-ylamino]-2-methyl-isoindole-1,3-dione,

Example 13-17

3-(2-bromo-6-fluoro-phenyl)-7-(3,3-dioxo-2,3-dihydro-3$\lambda^6$-benzo[1,3]oxathiol-5-ylamino)-1-methyl-3,4-dihydro-1H-pyrimido[4,5-d]pyrimidin-2-one

Example 13-18

3-(2-bromo-phenyl)-3,4-dihydro-7-(1'-ethyl-spiro[1,3-benzodioxolo-2,4'-piperidine]-5-yl)amino-1-methyl-pyrimido[4,5-d]pyrimidin-2(1H)-one,

Example 13-19

3-(2-bromo-phenyl)-7-(2,3-dihydro-benzo[1,4]oxathiin-7-ylamino)-1-methyl-3,4-dihydro-1H-pyrimido[4,5-d]pyrimidin-2-one,

Example 13-20

3-(2-bromo-phenyl)-1-methyl-7-(4-methyl-3-oxo-3,
4-dihydro-2H-benzo[1,4]thiazin-6-ylamino)-3,4-
dihydro-1H-pyrimido[4,5-d]pyrimidin-2-one,

Example 13-21

3-(2-bromo-phenyl)-1-methyl-7-(2-pyrrolidin-1-
ylmethyl-2,3-dihydro-benzo[1,4]dioxin-6-ylamino)-
3,4-dihydro-1H-pyrimido[4,5-d]pyrimidin-2-one
(mp: 201–203° C.),

Example 13-22

3-(2-bromo-phenyl)-7-(2-cyclopropylaminomethyl-
2,3-dihydro-benzo[1,4]dioxin-6-ylamino)-1-methyl-
3,4-dihydro-1H-pyrimido[4,5-d]pyrimidin-2-one,

Example 13-23

3-(2-bromo-6-fluoro-phenyl)-7-(2-hydroxymethyl-2,
3-dihydro-benzo[1,4]dioxin-6-ylamino)-1-methyl-3,
4-dihydro-1H-pyrimido[4,5-d]pyrimidin-2-one,

Example 13-24

3-(2-bromo-phenyl)-7-(4,4-dioxo-3,4-dihydro-2H-
$4\lambda^6$-benzo[1,4]oxathiin-7-ylamino)-1-methyl-3,4-
dihydro-1H-pyrimido[4,5-d]pyrimidin-2-one

Example 13-25

3-(2-bromo-6-fluoro-phenyl)-1-methyl-7-(4-methyl-
3-oxo-3,4-dihydro-2H-benzo[1,4]thiazin-6-
ylamino)-3,4-dihydro-1H-pyrimido[4,5-d]pyrimidin-
2-one,

Example 13-26

3-(2-bromo-phenyl)-1-methyl-7-(4-methyl-1,1-di-
oxo-1,2,3,4-tetrahydro-1lambda*6*-benzo[1,4]thi-
azin-7-ylamino)-3,4-dihydro-1H-pyrimido[4,5-d]
pyrimidin-2-one (mp: 250–251° C.),

Example 13-27

3-(2-bromo-phenyl)-7-(4,4-dioxo-3,4-dihydro-2H-
$4\lambda^6$-benzo[1,4]oxathiin-6-ylamino)-1-methyl-3,4-
dihydro-1H-pyrimido[4,5-d]pyrimidin-2-one

Example 13-28

3-(2-bromo-phenyl)-1-methyl-7-(4-methyl-1,1,3-
trioxo-1,2,3,4-tetrahydro-$1\lambda^6$-benzo[1,4]thiazin-7-
ylamino)-3,4-dihydro-1H-pyrimido[4,5-d]pyrimidin-
2-one

Example 13-29

3-(2-bromo-6-fluoro-phenyl)-1,1,3-trioxo-1,2,3,4-
tetrahydro-$1\lambda^6$-benzo[1,4]thiazin-7-ylamino)-3,4-
dihydro-1H-pyrimido[4,5-d]pyrimidin-2-one

Example 13-30

3-(2-bromo-phenyl)-3,4-dihydro-7-(1'-(2-methoxy-
ethyl)-spiro[1,3-benzodioxolo-2,4'-piperidine]-5-yl)
amino-1-methyl-pyrimido[4,5-d]pyrimidin-2(1H)-
one,

Example 13-31

3-(2-bromo-6-fluorophenyl)-3,4-dihydro-7-(1'-(2-
methoxyethyl)-spiro[1,3-benzodioxolo-2,4'-piperi-
dine]-5-yl)amino-1-methyl-pyrimido[4,5-d]pyrimi-
din-2(1H)-one,

Example 13-32

3-(2-bromo-6-fluoro-phenyl)-7-(2-dimethylaminom-
ethyl-2,3-dihydro-benzo[1,4]dioxin-6-ylamino)-1-
methyl-3,4-dihydro-1H-pyrimido[4,5-d]pyrimidin-2-
one,

Example 13-33

3-(2-bromo-phenyl)-3,4-dihydro-7-(1'-methyl-spiro
[1,3-benzodioxolo-2,4'-piperidine]-5-yl)amino-1-
methyl-pyrimido[4,5-d]pyrimidin-2(1H)-one,

Example 13-34

7-(benzo[1,3]dioxol-5-ylamino)-3-(2,4-dichloro-
phenyl)-1-(4-methoxy-phenyl)-3,4-dihydro-1H-py-
rimido[4,5-d]pyrimidin-2-one,

Example 13-35

3-(2-bromo-6-fluoro-phenyl)-3,4-dihydro-7-(1'-me-
thyl-spiro[1,3-benzodioxolo-2,4'-piperidine]-5-yl)
amino-1-methyl-pyrimido[4,5-d]pyrimidin-2(1H)-
one (mp: 191–195° C.),

Example 13-36

3-(2-bromo-phenyl)-3,4-dihydro-7-(1'-cyanomethyl-
spiro[1,3-benzodioxolo-2,4'-piperidine]-5-yl)amino-
1-methyl-pyrimido[4,5-d]pyrimidin-2(1H)-one,

Example 13-37

3-(2-bromo-phenyl)-1-methyl-7-(3-pyrrolidin-1-
ylmethyl-2,3-dihydro-benzo[1,4]dioxin-6-ylamino)-
3,4-dihydro-1H-pyrimido[4,5-d]pyrimidin-2-one,

Example 13-38

3-(2-bromo-6-fluoro-phenyl)-1-methyl-7-(3-pyrroli-
din-1-ylmethyl-2,3-dihydro-benzo[1,4]dioxin-6-
ylamino)-3,4-dihydro-1H-pyrimido[4,5-d]pyrimidin-
2-one,

Example 13-39

3-(2-bromo-phenyl)-1-methyl-7-(3-morpholin-4-
ylmethyl-2,3-dihydro-benzo[1,4]dioxin-6-ylamino)-
3,4-dihydro-1H-pyrimido[4,5-d]pyrimidin-2-one,

Example 13-40

3-(2-bromo-6-fluoro-phenyl)-1-methyl-7-(3-morpholin-4-ylmethyl-2,3-dihydro-benzo[1,4]dioxin-6-ylamino)-3,4-dihydro-1H-pyrimido[4,5-d]pyrimidin-2-one,

Example 13-41

3-(2-bromo-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one,

Example 13-42

3-(2-bromo-6-fluoro-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one,

Example 13-43

3-(2-bromo-phenyl)-7-(3-hydroxymethyl-2,3-dihydro-benzo[1,4]dioxin-6-ylamino)-1-methyl-3,4-dihydro-1H-pyrimido[4,5-d]pyrimidin-2-one,

Example 13-44

3-(2-bromo-6-fluoro-phenyl)-7-(3-hydroxymethyl-2,3-dihydro-benzo[1,4]dioxin-6-ylamino)-1-methyl-3,4-dihydro-1H-pyrimido[4,5-d]pyrimidin-2-one,

Example 13-45

3-(2-bromo-5-methoxyphenyl)-3,4-dihydro-7-(spiro[1,3-benzodioxolo-2,4'-piperidine]-5-yl)amino-1-methyl-pyrimido[4,5-d]pyrimidin-2(1H)-one,

Example 13-46

3-(2-bromo-6-fluoro-phenyl)-3,4-dihydro-7-(spiro[1,3-benzodioxolo-2,4'-piperidine]-5-yl)amino-1-methyl-pyrimido[4,5-d]pyrimidin-2(1H)-one, NMR (CDCl3, δ in ppm): 2.00 (m, 4 H); 3.07 (m, 4H); 3.45 (s, 3H); 4.58 (s, 2H); 6.71 (d, 1H); 6.83 (dd, 1H); 6.92 (s, 1H); 7.19 (m, 1H); 7.25 (m, 2H); 7.47 (dd, 1H); 7.96 (s, 1H); MS (APCI$^+$): 541 (M+1), mp: 146–153° C.

Example 13-47

2-[7-(4,4-Dioxo-3,4-dihydro-2H-4$\lambda^6$-benzo[1,4]oxathiin-6-ylamino)-1-methyl-2-oxo-1,4-dihydro-2H-pyrimido[4,5-d]pyrimidin-3-yl]-benzonitrile

Example 13-48

3-(2-Bromo-5-methoxy-phenyl)-7-(4,4-dioxo-3,4-dihydro-2H-4$\lambda^6$-benzo[1,4]oxathiin-6-ylamino)-1-methyl-3,4-dihydro-1H-pyrimido[4,5-d]pyrimidin-2-one

Example 13-49

7-(4,4-Dioxo-3,4-dihydro-2H-4$\lambda^6$-benzo[1,4]oxathiin-6-ylamino)-3-(2-fluoro-6-methoxy-phenyl)-1-methyl-3,4-dihydro-1H-pyrimido[4,5-d]pyrimidin-2-one

Example 13-50

3-(2-Bromo-phenyl)-7-(4,4-dioxo-3,4-dihydro-2H-4$\lambda^6$-benzo[1,4]oxathiin-6-ylamino)-1,4-dimethyl-3,4-dihydro-1H-pyrimido[4,5-d]pyrimidin-2-one; enantiomer 2

Example 13-51

3-(2-Bromo-phenyl)-1,4-dimethyl-7-(4-methyl-1,1,3-trioxo-1,2,3,4-tetrahydro-1$\lambda^6$-benzo[1,4]thiazin-7-ylamino)-3,4-dihydro-1H-pyrimido[4,5-d]pyrimidin-2-one; enantiomer 2

Example 13-52

3-(2-Bromo-phenyl)-1,4-dimethyl-7-(4-methyl-1,1,3-trioxo-1,2,3,4-tetrahydro-1$\lambda^6$-benzo[1,4]thiazin-7-ylamino)-3,4-dihydro-1H-pyrimido[4,5-d]pyrimidin-2-one; enantiomer 1

Example 13-53

2-[7-(4,4-Dioxo-3,4-dihydro-2H-4$\lambda^6$-benzo[1,4]oxathiin-6-ylamino)-1-methyl-2-oxo-1,4-dihydro-2H-pyrimido[4,5-d]pyrimidin-3-yl]-3-fluoro-benzonitrile.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

The invention claimed is:

1. A compound of formula I

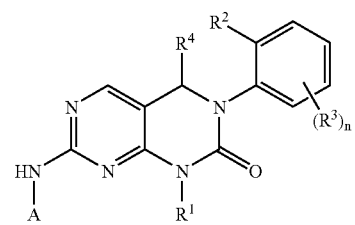

wherein $R^1$ represents hydrogen or alkyl, cycloalkyl, aryl, heteroaryl, arylalkyl or heteroarylalkyl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), —SO$_2$N(alkyl)$_2$;

$R^2$ represents halogen, cyano or $CF_3$;

$R^3$ each $R^3$ is independently selected from halogen, hydroxy, cyano, nitro, amino, acylamino, —$CONH_2$, —$SO_2NH_2$, —$S(O)_m$-alkyl, —NH-alkyl, —$N(alkyl)_2$, —CONH(alkyl), —$CON(alkyl)_2$, —$SO_2NH(alkyl)$, —$SO_2N(alkyl)_2$, or alkyl, alkoxy or alkoxyalkyl, each of which may be optionally substituted with halogen, hydroxy, cyano, nitro, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), $CON(alkyl)_2$, —$SO_2NH(alkyl)$, —$SO_2N(alkyl)_2$;

$R^4$ represents hydrogen, alkyl, alkoxy or cyano;

A is selected from the group

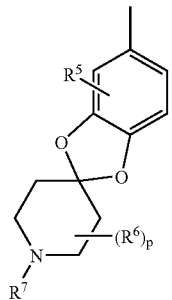
A-1

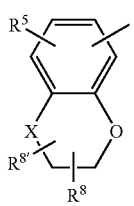
A-2

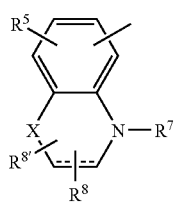
A-3

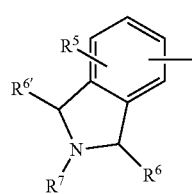
A-4

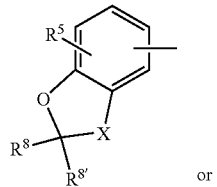
A-5

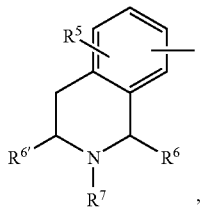
A-6

-continued $R^5$ is hydrogen, halogen, hydroxy, cyano, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), —$CON(alkyl)_2$, —$SO_2NH(alkyl)$ or —$SO_2N(alkyl)_2$;

$R^6$, $R^{6'}$ are each independently selected from hydrogen, alkyl or oxo;

$R^7$ is hydrogen, acyl, alkoxycarbonyl, alkoxyalkyl, alkyl or alkyl substituted with hydroxy, cyano, —$S(O)_m$-alkyl, amino, —NH-alkyl or —$N(alkyl)_2$;

$R^8$, $R^{8'}$ are each independently selected from hydrogen, oxo, alkoxy, alkoxyalkyl, alkyl or alkyl substituted with hydrogen, hydroxy, cyano, pyrrolidin-1-yl, morpholino, piperazin-1-yl, 4-alkyl-piperazin-1-yl, piperidin-1-yl, —$S(O)_m$-alkyl, or a group $NR^9R^{9'}$, provided that when either $R^8$ or $R^{8'}$ represent an oxo group, this oxo group is not adjacent to an $S(O)_m$ group;

$R^9$ and $R^{9'}$ are each independently selected from hydrogen, alkyl or cycloalkyl;

X is oxygen or $S(O)_m$;

the dashed line is an optional second chemical bond;

n is 0, 1 or 2;

m is 0, 1 or 2; and p is 0, 1 or 2;

or a pharmaceutically acceptable salt or N-oxides thereof.

2. A compound according to claim 1, wherein $R^1$ represents hydrogen or alkyl, cycloalkyl, aryl, heteroaryl, arylalkyl, or heteroarylalkyl, each of which may be optionally substituted with halogen, hydroxy, cyano, nitro, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), $CON(alkyl)_2$, —$SO_2NH(alkyl)$, or —$SO_2N(alkyl)_2$;

$R^2$ represents halogen, cyano or $CF_3$;

$R^3$ each $R^3$ is independently selected from halogen, hydroxy, cyano, nitro, amino, acylamino, —$CONH_2$, —$SO_2NH_2$, —$S(O)_m$-alkyl, —NH-alkyl, —$N(alkyl)_2$, —CONH(alkyl), —$CON(alkyl)_2$, —$SO_2NH(alkyl)$, —$SO_2N(alkyl)_2$, or alkyl, alkoxy or alkoxyalkyl, each of which may be optionally substituted with halogen, hydroxy, cyano, nitro, amino, acylamino, alkyl, alkoxy, alkoxyalkyl, —$CONH_2$, —$SO_2NH_2$, —$S(O)_m$-alkyl, —NH-alkyl, —$N(alkyl)_2$, —CONH(alkyl), $CON(alkyl)_2$, —$SO_2NH(alkyl)$, or —$SO_2N(alkyl)_2$;

$R^4$ represents hydrogen, alkyl, alkoxy or cyano;

43

A is selected from

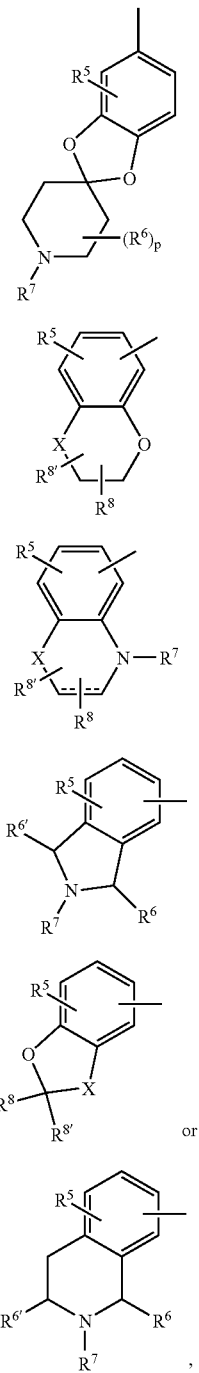

A-1

A-2

A-3

A-4

A-5

A-6

R⁵ is hydrogen, halogen, hydroxy, cyano, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), —CON(alkyl)$_2$, —SO$_2$NH(alkyl) or —SO$_2$N(alkyl)$_2$;

R⁶, R⁶' are each independently selected from hydrogen, alkyl or oxo;

R⁷ is hydrogen, acyl, alkoxycarbonyl, alkoxyalkyl, alkyl or

44 alkyl substituted with hydroxy, cyano, —S(O)$_m$-alkyl, amino, —NH-alkyl or —N(alkyl)$_2$;

R⁸, R⁸' are each independently selected from hydrogen, oxo, alkoxy, alkoxyalkyl, alkyl or alkyl substituted with hydrogen, cyano, pyrrolidin-1-yl, morpholino, piperazin-1-yl, 4-alkyl-piperazin-1-yl, piperidin-1-yl, —S(O)$_m$-alkyl, or a group NR⁹R⁹', provided that when either R⁸ or R⁸' represent an oxo group, this oxo group is not adjacent to an S(O)$_m$ group;

R⁹ and R⁹' are each independently selected from hydrogen, alkyl or cycloalkyl;

X is oxygen or S(O)$_m$;

the dashed line is an optional second chemical bond;

n is 0, 1 or 2;

m is 0, 1 or 2; and p is 0, 1 or 2;

or a pharmaceutically acceptable salt or N-oxides thereof.

3. The compound of claim 2 wherein R² is bromine and n=0.

4. The compound of claim 2 wherein n is 1 and R² and R³ are each independently selected from fluorine, chlorine, bromine or iodine.

5. The compound of claim 4 wherein R² is bromine and R³ is fluorine.

6. The compound of claim 5 wherein the R³ is at the 6-position of the phenyl ring.

7. The compound of claim 4 wherein R² and R³ are both chlorine.

8. The compound of claim 2, wherein

A is selected from A-1, A-2, A-3, A-4, A-5 or A-6;

R¹ is alkyl or aryl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), or —SO$_2$N(alkyl)$_2$;

R² is halogen or cyano;

R³ each R³ is independently selected from halogen;

n is 0 or 1;

m is 0, 1 or 2;

R⁵ is hydrogen; and

R⁴ hydrogen or methyl; or a pharmaceutically acceptable salt thereof.

9. The compound according to claim 8 selected from 7-(Benzo[1,3]dioxol-5-ylamino)-3-(2,4-dichloro-phenyl)-1-(4-methoxy-phenyl)-3,4-dihydro-1H-pyrimido[4,5-d]pyrimidin-2-one; and 2-[7-(4,4-Dioxo-3,4-dihydro-2H-4λ⁶-benzo[1,4]oxathiin-6-ylamino)-1-methyl-2-oxo-1,4-dihydro-2H-pyrimido[4,5-d]pyrimidin-3-yl]-benzonitrile.

10. The compound of claim 2 wherein

A is A-1;

R⁵ is hydrogen;

p is 0;

R¹ is alkyl;

R² is halogen;

R³ is halogen;

n is 0 or 1; and

R⁴ is hydrogen;

or a pharmaceutically acceptable salt thereof.

11. The compound according to claim 10 which is selected from 3-(2-bromo-phenyl)-3,4-dihydro-7-(1'-acetyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one, 3-(2-bromo-6-fluorophenyl)-3,4-dihydro-7-(1'-acetyl-spiro[1,3-benzodioxolo-2,4'-piperidine]-5-yl)amino-1-methyl-pyrimido[4,5-d]pyrimidin-2(1H)-one, 3-(2-bromo-6-fluorophenyl)-3,4-dihydro-7-(1'-ethoxycarbonyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-ethyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-(2-methoxyethyl)-spiro[1,3-benzodioxolo-2,4'-piperidine]-5-yl)amino-1-methyl-pyrimido[4,5-d]pyrimidin-2(1H)-one, and 3-(2-bromo-6-fluorophenyl)-3,4-dihydro-7-(1'-(2-methoxyethyl)-spiro[1,3-benzodioxolo-2,4'-piperidine]-5-yl)amino-1-methyl-pyrimido[4,5-d]pyrimidin-2(1H)-one.

12. The compound according to claim 10 which is selected from 3-(2-bromo-phenyl)-3,4-dihydro-7-(spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-methyl-spiro[1,3-benzodioxolo-2,4'-piperidine]-5-yl)amino-1-methyl-pyrimido[4,5-d]pyrimidin-2(1H)-one, 3-(2-bromo-6-fluoro-phenyl)-3,4-dihydro-7-(spiro[1,3-benzodioxolo-2,4'-piperidine]-5-yl)amino-1-methyl-pyrimido[4,5-d]pyrimidin-2(1H)-one, 3-(2-bromo-6-fluoro-phenyl)-3,4-dihydro-7-(1'-methyl-spiro[1,3-benzodioxolo-2,4'-piperidine]-5-yl)amino-1-methyl-pyrimido[4,5-d]pyrimidin-2(1H)-one, 3-(2-bromo-phenyl)-3,4-dihydro-7-(1'-cyanomethyl-spiro[1,3-benzodioxolo-2,4'-piperidine]-5-yl)amino-1-methyl-pyrimido[4,5-d]pyrimidin-2(1H)-one, and 3-(2-bromo-5-methoxyphenyl)-3,4-dihydro-7-(spiro[1,3-benzodioxolo-2,4'-piperidine]-5-yl)amino-1-methyl-pyrimido[4,5-d]pyrimidin-2(1H)-one.

13. The compound according to claim 2 wherein
A is a group A-2;
$R^5$ is hydrogen;
X is oxygen;
$R^8$, $R^{8'}$ are each independently selected from hydrogen or alkyl that optionally may be substituted with cyano, pyrrolidin-1-yl, morpholino, piperazin-1-yl, 4-alkyl-piperazin-1-yl, piperidin-1-yl, —S(O)$_m$-alkyl, or a group NR$^9$R$^{9'}$;
$R^9$ and $R^{9'}$ are each independently selected from hydrogen, alkyl or cycloalkyl;
$R^1$ is alkyl;
$R^2$ is halogen;
$R^3$ is halogen;
n is 0 or 1; and
$R^4$ is hydrogen;
or a pharmaceutically acceptable salt thereof.

14. The compound according to claim 13, which is selected from 3-(2-bromo-phenyl)-7-(2,3-dihydro-benzo[1,4]dioxin-6-ylamino)-1-methyl-3,4-dihydro-1H-pyrimido[4,5-d]pyrimidin-2-one, 3-(2-bromo-phenyl)-1-methyl-7-(2-pyrrolidin-1-ylmethyl-2,3-dihydro-benzo[1,4]dioxin-6-ylamino)-3,4-dihydro-1H-pyrimido[4,5-d]pyrimidin-2-one, 3-(2-bromo-phenyl)-1-methyl-7-(3-pyrrolidin-1-ylmethyl-2,3-dihydro-benzo[1,4]dioxin-6-ylamino)-3,4-dihydro-1H-pyrimido[4,5-d]pyrimidin-2-one, 3-(2-bromo-phenyl)-7-(2-dimethylaminomethyl-2,3-dihydro-benzo[1,4]dioxin-6-ylamino)-1-methyl-3,4-dihydro-1H-pyrimido[4,5-d]pyrimidin-2-one, 3-(2-bromo-6-fluoro-phenyl)-7-(2-dimethylaminomethyl-2,3-dihydro-benzo[1,4]dioxin-6-ylamino)-1-methyl-3,4-dihydro-1H-pyrimido[4,5-d]pyrimidin-2-one, 3-(2-bromo-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one, 3-(2-bromo-6-fluoro-phenyl)-7-(3-dimethylaminomethyl-2,3-dihydro-benzo[1,4]dioxin-6-ylamino)-1-methyl-3,4-dihydro-1H-pyrimido[4,5-d]pyrimidin-2-one, 3-(2-bromo-phenyl)-7-(2-cyclopropylaminomethyl-2,3-dihydro-benzo[1,4]dioxin-6-ylamino)-1-methyl-3,4-dihydro-1H-pyrimido[4,5-d]pyrimidin-2-one, 3-(2-bromo-phenyl)-1-methyl-7-(2-morpholin-4-ylmethyl-2,3-dihydro-benzo[1,4]dioxin-6-ylamino)-3,4-dihydro-1H-pyrimido[4,5-d]pyrimidin-2-one, 3-(2-bromo-phenyl)-1-methyl-7-(3-morpholin-4-ylmethyl-2,3-dihydro-benzo[1,4]dioxin-6-ylamino)-3,4-dihydro-1H-pyrimido[4,5-d]pyrimidin-2-one, 3-(2-bromo-6-fluoro-phenyl)-1-methyl-7-(3-morpholin-4-ylmethyl-2,3-dihydro-benzo[1,4]dioxin-6-ylamino)-3,4-dihydro-1H-pyrimido[4,5-d]pyrimidin-2-one, and 3-(2-bromo-6-fluoro-phenyl)-1-methyl-7-(3-pyrrolidin-1-ylmethyl-2,3-dihydro-benzo[1,4]dioxin-6-ylamino)-3,4-dihydro-1H-pyrimido[4,5-d]pyrimidin-2-one.

15. The compound according to claim 1 wherein
A is a group A-2;
$R^5$ is hydrogen;
X is oxygen;
$R^8$ is hydrogen
$R^{8'}$ is alkyl substituted with hydroxy;
$R^1$ is alkyl;
$R^2$ is halogen;
$R^3$ is halogen;
n is 0 or 1; and
$R^4$ is hydrogen;
or a pharmaceutically acceptable salt thereof.

16. The compound according to claim 15, which is selected from 3-(2-bromo-phenyl)-7-(2-hydroxymethyl-2,3-dihydro-benzo[1,4]dioxin-6-ylamino)-1-methyl-3,4-dihydro-1H-pyrimido[4,5-d]pyrimidin-2-one, 3-(2-bromo-phenyl)-7-(3-hydroxymethyl-2,3-dihydro-benzo[1,4]dioxin-6-ylamino)-1-methyl-3,4-dihydro-1H-pyrimido[4,5-d]pyrimidin-2-one, 3-(2-bromo-6-fluoro-phenyl)-7-(3-hydroxymethyl-2,3-dihydro-benzo[1,4]dioxin-6-ylamino)-1-methyl-3,4-dihydro-1H-pyrimido[4,5-d]pyrimidin-2-one, and 3-(2-bromo-6-fluoro-phenyl)-7-(2-hydroxymethyl-2,3-dihydro-benzo[1,4]dioxin-6-ylamino)-1-methyl-3,4-dihydro-1H-pyrimido[4,5-d]pyrimidin-2-one.

17. The compound of claim 2 wherein
A is A-2;
$R^5$ is hydrogen;
X is S(O)$_m$;
m is 0, 1 or 2;
$R^8$, $R^{8'}$ are hydrogen;
$R^1$ is alkyl;
$R^2$ is halogen;
$R^3$ is halogen;
n is 0 or 1; and
$R^4$ is hydrogen;
or a pharmaceutically acceptable salt thereof.

18. The compound according to claim 17, which is selected from 3-(2-bromo-phenyl)-7-(2,3-dihydro-benzo[1,4]oxathiin-7-ylamino)-1-methyl-3,4-dihydro-1H-pyrimido[4,5-d]pyrimidin-2-one, 3-(2-bromo-phenyl)-7-(4,4-dioxo-3,4-dihydro-2H-4$\lambda^6$-benzo[1,4]oxathiin-7-ylamino)-1-methyl-3,4-dihydro-1H-pyrimido[4,5-d]pyrimidin-2-one, 3-(2-bromo-6-fluoro-phenyl)-7-(4,4-dioxo-3,4-dihydro-2H-4$\lambda^6$-benzo[1,4]oxathiin-6-ylamino)-1-methyl-3,4-dihydro-1H-pyrimido[4,5-d]pyrimidin-2-one, and 3-(2-bromo-phenyl)-7-(4,4-dioxo-3,4-dihydro-2H-4$\lambda^6$-benzo[1,4]oxathiin-6-ylamino)-1-methyl-3,4-dihydro-1H-pyrimido[4,5-d]pyrimidin-2-one.

19. The compound of claim 2 wherein

A is A-3;

$R^5$ is hydrogen;

$R^7$ is hydrogen or alkyl;

X is $S(O)_m$;

m is 0, 1 or 2;

$R^8$, $R^{8'}$ are each independently selected from hydrogen, oxo or alkoxy, provided that when one of $R^8$, $R^{8'}$ is oxo the dashed line is absent, and provided further that when $R^8$ and $R^{8'}$ are selected from hydrogen or alkoxy the dashed line may represent an additional bond to form a double bond;

$R^1$ is alkyl;

$R^2$ is halogen;

$R^3$ is halogen;

n is 0 or 1; and $R^4$ is hydrogen;

or a pharmaceutically acceptable salt thereof.

20. The compound according to claim 19 which is selected from 3-(2-bromo-phenyl)-1-methyl-7-(3-oxo-3,4-dihydro-2H-benzo[1,4]thiazin-7-ylamino)-3,4-dihydro-1H-pyrimido[4,5-d]pyrimidin-2-one, 3-(2-bromo-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one, 3-(2-bromo-phenyl)-1-methyl-7-(4-methyl-1,3-dioxo-1,2 3,4-tetrahydro-1I$\lambda^4$-benzo[1,4]thiazin-7-ylamino)-3,4-dihydro-1H-pyrimido[4,5-d]pyrimidin-2-one, 3-(2-bromo-phenyl)-1-methyl-7-(4-methyl-3,4-dihydro-2H-benzo[1,4]thiazin-7-ylamino)-3,4-dihydro-1H-pyrimido[4,5-d]pyrimidin-2-one, 3-(2-bromo-phenyl)-1-methyl-7-(3-oxo-3,4-dihydro-2H-benzo[1,4]thiazin-6-ylamino)-3,4-dihydro-1H-pyrimido[4,5-d]pyrimidin-2-one, 3-(2-bromo-6-fluoro-phenyl)-1-methyl-7-(4-methyl-3-oxo-3,4-dihydro-2H-benzo[1,4]thiazin-7-ylamino)-3,4-dihydro-1H-pyrimido[4,5-d]pyrimidin-2-one, and 3-(2-bromo-6-fluoro-phenyl)-1-methyl-7-(3-oxo-3,4-dihydro-2H-benzo[1,4]thiazin-6-ylamino)-3,4-dihydro-1H-pyrimido[4,5-d]pyrimidin-2-one.

21. The compound according to claim 19 which is selected from 3-(2-bromo-phenyl)-1-methyl-7-(4-methyl-3-oxo-3,4-dihydro-2H-benzo[1,4]thiazin-6-ylamino)-3,4-dihydro-1H-pyrimido[4,5-d]pyrimidin-2-one, 3-(2-bromo-phenyl)-7-(3-methoxy-4-methyl-1-oxo-1,4-dihydro-1$\lambda^4$-benzo[1,4]thiazin-7-ylamino)-1-methyl-3,4-dihydro-1H-pyrimido[4,5-d]pyrimidin-2-one, 3-(2-bromo-6-fluoro-phenyl)-1-methyl-7-(4-methyl-3-oxo-3,4-dihydro-2H-benzo[1,4]thiazin-6-ylamino)-3,4-dihydro-1H-pyrimido[4,5-d]pyrimidin-2-one, 3-(2-bromo-6-fluoro-phenyl)-1-methyl-7-(4-methyl-1,1-dioxo-1,2,3,4-tetrahydro-1$\lambda^6$-benzo[1,4]thiazin-7-ylamino)-3,4-dihydro-1H-pyrimido[4,5-d]pyrimidin-2-one, 3-(2-bromo-phenyl)-1-methyl-7-(4-methyl-1,1-dioxo-1,2,3,4-tetrahydro-1$\lambda^6$-benzo[1,4]thiazin-7-ylamino)-3,4-dihydro-1H-pyrimido[4,5-d]pyrimidin-2-one, 3-(2-bromo-phenyl)-1-methyl-7-(4-methyl-1,1,3-trioxo-1,2,3,4-tetrahydro-1$\lambda^6$-benzo[1,4]thiazin-7-ylamino)-3,4-dihydro-1H-pyrimido[4,5-d]pyrimidin-2-one, and 3-(2-bromo-6-fluoro-phenyl)-1-methyl-7-(4-methyl-1,1,3-trioxo-1,2,3,4-tetrahydro-1$\lambda^6$-benzo[1,4]thiazin-7-ylamino)-3,4-dihydro-1H-pyrimido[4,5-d]pyrimidin-2-one.

22. The compound of claim 2, wherein

A is A-4;

$R^5$ is hydrogen;

$R^6$, $R^{6'}$ are each independently selected from hydrogen or oxo;

$R^7$ is hydrogen or alkyl that optionally may be substituted with hydroxy, cyano, —$S(O)_m$-alkyl, amino, —NH-alkyl or —$N(alkyl)_2$;

$R^1$ is alkyl;

$R^2$ is halogen;

$R^3$ is halogen;

n is 0 or 1;

m is 0, 1 or 2;

$R^4$ is hydrogen;

or a pharmaceutically acceptable salts thereof.

23. The compound according to claim 22 which is selected from

5-[6-(2-bromo-phenyl)-8-methyl-7-oxo-5,6,7,8-tetrahydro-pyrimido[4,5-d]pyrimidin-2-ylamino]-2-methyl-isoindole-1,3-dione, 3-(2-bromo-phenyl)-1-methyl-7-(2-methyl-2,3-dihydro-1H-isoindol-5-ylamino)-3,4-dihydro-1H-pyrimido[4,5-d]pyrimidin-2-one; hydrochloride salt, 5-[6-(2-bromo-phenyl)-8-methyl-7-oxo-5,6,7,8-tetrahydro-pyrimido[4,5-d]pyrimidin-2-ylamino]-isoindole-1,3-dione, 5-[6-(2-bromo-6-fluoro-phenyl)-8-methyl-7-oxo-5,6,7,8-tetrahydro-pyrimido[4,5-d]pyrimidin-2-ylamino]-2-methyl-isoindole-1,3-dione, and 3-(2-bromo-6-fluoro-phenyl)-7-[2-(2-hydroxy-1,1-dimethyl-ethyl)-2,3-dihydro-1H-isoindol-5-ylamino]-1-methyl-3,4-dihydro-1H-pyrimido[4,5-d]pyrimidin-2-one; hydrochloride.

24. The compound of claim 2, wherein

A is A-5;

$R^5$ is hydrogen;

X is oxygen;

$R^8$, $R^{8'}$ are each independently selected from hydrogen or alkyl;

$R^1$ is alkyl;

$R^2$ is halogen;

$R^3$ is halogen;

n is 0 or 1; and $R^4$ is hydrogen; or a pharmaceutically acceptable salt thereof.

25. The compound according to claim 24 which is 7-(benzo[1,3]dioxol-5-ylamino)-3-(2-bromo-phenyl)-1-methyl-3,4-dihydro-1H-pyrimido[4,5-d]pyrimidin-2-one.

26. A compound of claim 2, wherein

A is A-5';

$R^5$ is hydrogen;

X is $S(O)_m$;

m is 0, 1 or 2;

R⁸, R⁸' are each independently selected from hydrogen or alkyl;
$R^1$ is alkyl;
$R^2$ is halogen;
$R^3$ is halogen;
n is 0 or 1; and
$R^4$ is hydrogen; or
a pharmaceutically acceptable salt thereof.

27. The compound according to claim 26 which is selected from
   3-(2-bromo-6-fluoro-phenyl)-7-(3,3-dioxo-2,3-dihydro-3λ⁶-benzo[1,3]oxathiol-5-ylamino)-1-methyl-3,4-dihydro-1H-pyrimido[4,5-d]pyrimidin-2-one, and
   3-(2-bromo-phenyl)-7-(3,3-dioxo-2,3-dihydro-3λ⁶-benzo[1,3]oxathiol-5-ylamino)-1-methyl-3,4-dihydro-1H-pyrimido[4,5-d]pyrimidin-2-one.

28. The compound of claim 2, wherein
A is A-6,
$R^5$ is hydrogen;
$R^1$ is alkyl;
$R^2$ is halogen;
$R^3$ is halogen;
n is 0 or 1; and
$R^4$ is hydrogen; or
a pharmaceutically acceptable salt thereof.

29. The compound according to claim 28 which is selected from
   3-(2-Bromo-5-methoxy-phenyl)-7-(4,4-dioxo-3,4-dihydro-2H-4λ⁶-benzo[1,4]oxathiin-6-ylamino)-1-methyl-3,4-dihydro-1H-pyrimido[4,5-d]pyrimidin-2-one,
   7-(4,4-Dioxo-3,4-dihydro-2H-4λ⁶-benzo[1,4]oxathiin-6-ylamino)-3-(2-fluoro-6-methoxy-phenyl)-1-methyl-3,4-dihydro-1H-pyrimido[4,5-d]pyrimidin-2-one,
   3-(2-Bromo-phenyl)-7-(4,4-dioxo-3,4-dihydro-2H-4λ⁶-benzo[1,4]oxathiin-6-ylamino)-1,4-dimethyl-3,4-dihydro-1H-pyrimido[4,5-d]pyrimidin-2-one; enantiomer 1,
   3-(2-Bromo-phenyl)-7-(4,4-dioxo-3,4-dihydro-2H-4λ⁶-benzo[1,4]oxathiin-6-ylamino)-1,4-dimethyl-3,4-dihydro-1H-pyrimido[4,5-d]pyrimidin-2-one; enantiomer 2,
   3-(2-Bromo-phenyl)-1,4-dimethyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one; enantiomer 2,
   3-(2-Bromo-phenyl)-1,4-dimethyl-7-(4-methyl-1,1,3-trioxo-1,2,3,4-tetrahydro-1λ⁶-benzo[1,4]thiazin-7-ylamino)-3,4-dihydro-1H-pyrimido[4,5-d]pyrimidin-2-one; enantiomer 1, and
   2-[7-(4,4-Dioxo-3,4-dihydro-2H-4λ⁶-benzo[1,4]oxathiin-6-ylamino)-1-methyl-2-oxo-1,4-dihydro-2H-pyrimido[4,5-d]pyrimidin-3-yl]-3-fluoro-benzonitrile.

30. A compound of the formula A-1-I,

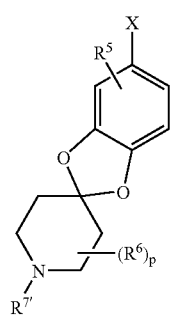

A-1-I wherein
$R^5$ is hydrogen, halogen, hydroxy, cyano, amino, acylamino, alkyl, alkoxy, alkoxyalkyl, —CONH₂, —SO₂NH₂, —S(O)ₘ-alkyl, —NH-alkyl, —N(alkyl)₂, —CONH(alkyl), —CON(alkyl)₂, —SO₂NH(alkyl) or —SO₂N(alkyl)₂;

$R^6$ each $R^6$ is independently selected from hydrogen, alkyl or oxo;

$R^7$ is hydrogen, acyl, alkoxycarbonyl, alkoxyalkyl, alkyl or
   alkyl substituted with hydroxy, cyano, —S(O)ₘ-alkyl, amino, —NH-alkyl or —N(alkyl)₂;

m is 0, 1 or 2;

p is 0, 1 or 2; and

X is NO₂ or an optionally protected NH₂ group.

31. A pharmaceutical composition comprising a compound of formula I and a pharmaceutically acceptable adjuvant.

32. A process for the preparation of a compound of formula I comprising
   reacting a compound of formula

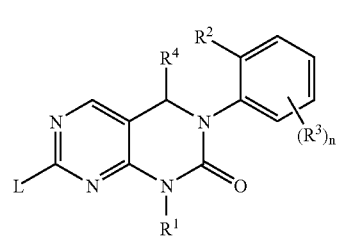

(II)

wherein
$R^1$ represents hydrogen or
   alkyl, cycloalkyl, aryl, heteroaryl, arylalkyl, or heteroarylalkyl, each of which may be optionally substituted with halogen, hydroxy, cyano, nitro, amino, acylamino, alkyl, alkoxy, alkoxyalkyl, —CONH₂, —SO₂NH₂, —S(O)ₘ-alkyl, —NH-alkyl, —N(alkyl)₂, —CONH(alkyl), CON(alkyl)₂, —SO₂NH(alkyl), or —SO₂N(alkyl)₂;

$R^2$ represents halogen, cyano or CF₃;

$R^3$ each $R^3$ is independently selected from halogen, hydroxy, cyano, nitro, amino, acylamino, —CONH₂, —SO₂NH₂, —S(O)ₘ-alkyl, —NH-alkyl, —N(alkyl)₂, —CONH(alkyl), —CON(alkyl)₂, —SO₂NH(alkyl), —SO₂N(alkyl)₂, or
   alkyl, alkoxy or alkoxyalkyl, each of which may be optionally substituted with halogen, hydroxy, cyano, nitro, amino, acylamino, alkyl, alkoxy, alkoxyalkyl, —CONH₂, —SO₂NH₂, —S(O)ₘ-alkyl, —NH-alkyl, —N(alkyl)₂, —CONH(alkyl), CON(alkyl)₂, —SO₂NH(alkyl), or —SO₂N(alkyl)₂;

$R^4$ represents hydrogen, alkyl, alkoxy or cyano; and

L signifies a group selected from benzylsulphonyl, phenylsulphonyl, alkanesulphonyl, p-tolylsulfonyloxy, methanesulfonyloxy, trifluoromethanesulfonyloxy, chloro, bromo, iodo, and fluoro;
   with an amine of the formula

wherein A is selected from

A-1

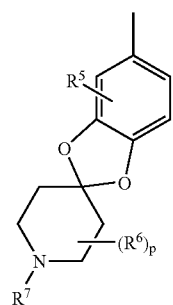

A-2

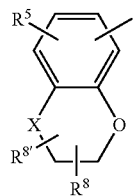

A-3

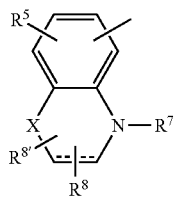

A-4

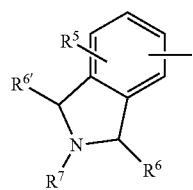

A-5

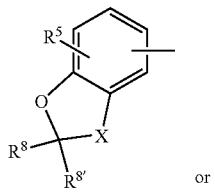

or

A-6

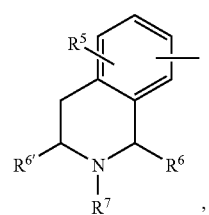

, and $R^5$, $R^6$, $R^{6'}$, $R^7$, $R^8$, $R^{8'}$ and p have the meanings given in claim 2.

33. The process of claim 32 wherein the group L is selected from methanesulfonyloxy and iodo.

34. A process for the preparation of a compound of formula I, comprising (a) reacting a compound of formula II

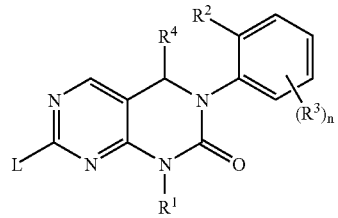

with ammonia or protected ammonia;

(b) cleaving any optional protecting group from the resulting compound of step (a) to give a compound of formula (IV);

(IV)

(structure IV as depicted)

and (c) reacting the compound of formula (IV) with a bicyclic compound of formula $$\underset{A}{\overset{L'}{|}}$$ (V)

wherein, in the above formulas $R^1$ represents hydrogen or
alkyl, cycloalkyl, aryl, heteroaryl, arylalkyl, or heteroarylalkyl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), or —SO$_2$N(alkyl)$_2$;

$R^2$ represents halogen, cyano or CF$_3$;

$R^3$ each $R^3$ is independently selected from halogen, hydroxy, cyano, nitro, amino, acylamino, —CONH$_2$, —SO$_2$NH$_2$, —S(O)$_m$-alkyl, —NH-alkyl, —N(alkyl)$_2$, —CONH(alkyl), —CON(alkyl)$_2$, —SO$_2$NH(alkyl), —SO$_2$N(alkyl)$_2$, or alkyl, alkoxy or alkoxyalkyl, each of which may be optionally substituted with halogen, hydroxy, cyano, nitro, amino, acylamino, alkyl, alkoxy, alkoxyalkyl, —CONH$_2$, —SO$_2$NH$_2$, —S(O)$_m$-alkyl, —NH-alkyl, —N(alkyl)$_2$, —CONH(alkyl), CON(alkyl)$_2$, —SO$_2$NH(alkyl), or —SO$_2$N(alkyl)$_2$;

R⁴ represents hydrogen, alkyl, alkoxy or cyano;
n is 0, 1 or 2;
m is 0, 1 or 2;
L and L' independently represent a group selected from benzylsulphonyl, phenylsulphonyl, alkanesulphonyl, p-tolylsulfonyloxy, methanesulfonyloxy, trifluoromethanesulfonyloxy, chloro, bromo, iodo, and fluoro; and
A has the meaning given in claim 2.

35. The process of claim 34 wherein the group L' is selected from iodo and methanesulfonyloxy.

36. The process of claim 34 wherein the reaction of Compound (IV) with Compound (V) may be catalyzed by a transition metal catalyst.

37. The process of claim 34 further comprising converting a basic compound of formula I synthesis into a pharmaceutically acceptable salt using an acid, or converting an acidic compound of formula I into a pharmaceutically acceptable salt using a base.

38. The process of claim 34 further comprising converting the resulting compound of formula I into a an N-oxide by oxidation with an oxidizing agent.

39. The process of claim 38 wherein the oxidizing agent is selected from 3-chloro-perbenzoic acid, trifluoroperacetic acid, or dimethyldioxiran.

* * * * *

UNITED STATES PATENT AND TRADEMARK OFFICE
CERTIFICATE OF CORRECTION

| | | |
|---|---|---|
| PATENT NO. | : 7,091,345 B2 | Page 1 of 1 |
| APPLICATION NO. | : 10/697543 | |
| DATED | : August 15, 2006 | |
| INVENTOR(S) | : Cai et al. | |

It is certified that error appears in the above-identified patent and that said Letters Patent is hereby corrected as shown below:

Title Page: Item 74

-The Attorney information reads: "Attorney, Agent, or Firm - George W. Johnston; Patricia S. Rooha-Tramaloni". The Attorney information should read -- George W. Johnston; Patricia S. Rocha-Tramaloni --.

Signed and Sealed this

Thirteenth Day of March, 2007

JON W. DUDAS
*Director of the United States Patent and Trademark Office*